(12) United States Patent
Burbank et al.

(10) Patent No.: US 12,733,928 B2
(45) Date of Patent: Sep. 15, 2026

(54) TRANSMISSION ASSEMBLY FOR DRIVING INSTRUMENT MOTION, AND RELATED DEVICES, SYSTEMS AND METHODS

(71) Applicant: INTUITIVE SURGICAL OPERATIONS, INC., Sunnyvale, CA (US)

(72) Inventors: William A. Burbank, Sandy Hook, CT (US); Matthew Aaron Wixey, Rochester, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 19/078,607

(22) Filed: Mar. 13, 2025

(65) Prior Publication Data

US 2025/0288291 A1 Sep. 18, 2025

Related U.S. Application Data

(60) Provisional application No. 63/565,170, filed on Mar. 14, 2024.

(51) Int. Cl.

| | |
|---|---|
| ***A61B 17/068*** | (2006.01) |
| ***A61B 17/00*** | (2006.01) |
| ***A61B 34/35*** | (2016.01) |
| ***B25J 9/10*** | (2006.01) |

(52) U.S. Cl.
CPC ............ *A61B 17/068* (2013.01); *A61B 34/35* (2016.02); *B25J 9/104* (2013.01); *A61B 2017/00398* (2013.01)

(58) Field of Classification Search
CPC .................. A61B 17/068; A61B 34/35; A61B 2017/00398; B25J 9/104
See application file for complete search history.

(56) References Cited

U.S. PATENT DOCUMENTS

| | | | | |
|---|---|---|---|---|
| 5,649,956 A * | 7/1997 | Jensen | B25J 18/04 | 606/1 |
| 5,807,378 A * | 9/1998 | Jensen | B25J 15/04 | 606/1 |
| 6,949,106 B2 * | 9/2005 | Brock | A61B 17/0469 | 606/130 |

(Continued)

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Michelle Lopez
(74) *Attorney, Agent, or Firm* — Jones Burke, PLLC

(57) ABSTRACT

A medical instrument comprises an instrument shaft, a movable component coupled to the instrument shaft, a rotational actuation element extending through the instrument shaft and operably coupled to the movable component, and a transmission assembly movably coupled to the instrument shaft. The transmission assembly comprises a first drive member configured to drive translation of the instrument shaft relative to the transmission assembly, and a second drive member coupled to the rotational actuation element and configured to drive rotation of the rotational actuation element. Translation of the instrument shaft relative to the transmission assembly causes translation of the rotational actuation element relative to the transmission assembly.

20 Claims, 19 Drawing Sheets

(56) References Cited

U.S. PATENT DOCUMENTS

| | | | | |
|---|---|---|---|---|
| 8,151,661 | B2 | 4/2012 | Schena et al. | |
| 9,055,961 | B2 | 6/2015 | Manzo et al. | |
| 10,470,830 | B2 | 11/2019 | Hill et al. | |
| 11,974,742 | B2 * | 5/2024 | Shelton, IV | A61B 34/30 |
| 2014/0276719 | A1 * | 9/2014 | Parihar | A61B 34/30 606/1 |
| 2016/0157945 | A1 * | 6/2016 | Madhani | B25J 3/04 606/130 |
| 2019/0038282 | A1 * | 2/2019 | Shelton, IV | A61B 34/70 |
| 2019/0239877 | A1 | 8/2019 | Ragosta et al. | |
| 2019/0239967 | A1 | 8/2019 | Ragosta et al. | |
| 2020/0237423 | A1 | 7/2020 | Witte et al. | |
| 2021/0093408 | A1 | 4/2021 | Carey et al. | |
| 2022/0387031 | A1 * | 12/2022 | Yates | A61B 17/07207 |
| 2023/0000578 | A1 * | 1/2023 | Moubarak | A61B 34/71 |

* cited by examiner proximal
distal 300
100
110
310
311
317
318
319
400_1
400_2
400_3
400_4
400_5
400_6
410
415
420
420'
430
431
432
433
434
440
450
451a
451b
452
500_1
500_2
500_3
500_4
500_5
530

TRANSMISSION ASSEMBLY FOR DRIVING INSTRUMENT MOTION, AND RELATED DEVICES, SYSTEMS AND METHODS

CROSS-REFERENCE TO RELATED APPLICATIONS

This application claims priority to U.S. Provisional Application No. 63/565,170, filed Mar. 14, 2024, which is incorporated herein by reference in its entirety.

FIELD

Aspects of this disclosure relate to instrument transmission assembly architectures, and related devices and methods, that provide a drive for degrees of freedom of motion of the instrument motion, such as instrument insertion and motion of movable components of the instrument. Aspects of the disclosure relate further to such instrument transmission assemblies for instruments configured for use with computer-assisted teleoperated manipulator systems.

INTRODUCTION

Some remotely-controlled instruments comprise a shaft, an end effector coupled to one end portion of the shaft, and a transmission assembly coupled along a portion of the shaft to provide forces transmitted along the shaft that control the end effector. In this way, the transmission assembly can remain outside a patient's body or other worksite region to control operations of an end effector performing functions at the desired worksite region. The end effector generally comprises one or more functional elements, such as, for example, a jaw mechanism, a stapler, a cutting implement, a camera, an electrode, a sensor, etc., to perform one or more functions of the instrument, such as cutting, sealing, grasping, imaging, etc. The transmission assembly may comprise one or more drive members configured to receive driving forces, torques, or other inputs and transmit the received driving forces, torques, or other inputs to other portions of the instrument, such as the end effector and/or other structures along portions of the shaft (e.g., joints and or wrist mechanisms), to drive degrees of freedom of motion and/or functions of the instrument. The drive members may transmit received driving forces or torques to other portions of the instrument via actuation elements running from the transmission assembly along the instrument shaft. Such actuation elements may be in the form of pulling (tension) members such as cables, wires, filaments or the like that are flexible in all directions and generally transmit stronger force by pulling on the actuation element to place it in tension (sometimes referred to as pull-pull actuation elements); more rigid members such as tubes, rods, sheet metal strips, or the like that can transmit force by pushing or by pulling on the actuation element (sometimes referred to as push-pull actuation elements); semi-flexible pushing members such as push coils that can transmit force by pushing while providing lateral flexibility; rotatable members such as lead screws that can transmit rotational force; and a variety of other forms of actuation elements. In some cases, the drive members may convert received driving forces or torques from one form to another, such as, for example, converting received torques into a linear forces. Further, in some cases, combinations of the various types of actuation elements can be used depending on the nature of the force needed and/or the flexibility desired as an actuation element is routed from the transmission assembly, along the shaft, to a moveable component (such as an articulable structure and/or a component of the end effector).

The transmission assembly of such instruments can be configured to be coupled to computer-assisted teleoperated manipulator systems to receive the drive inputs, such as via servo-motor and drive disk interfaces, and/or may be configured to receive input manually, such as via a user operating a wheel, button, trigger, or other mechanism at the force transmission assembly to provide the desired input.

Some remotely-controlled instruments have a degree of freedom of motion comprising linear translation of the instrument shaft relative to a workspace (e.g., a patient's body) along a longitudinal axis of the shaft. Such translation of the instrument shaft, and hence the end effector coupled thereto, may allow for insertion of the end effector into (or advancement further into) the workspace and withdrawal of the end effector from the workspace. This degree of freedom of motion may be referred to herein as an insertion degree of freedom, and the direction along which the translation occurs may be referred to herein as an insertion axis.

Some instruments, and manipulator systems, provide for the insertion degree of freedom of motion by translating the entire instrument, including the transmission assembly, along the insertion axis. For example, for a teleoperated manipulator system, an instrument holder to which the instrument is coupled, may be translatable along a link of a manipulator of the manipulator system. Likewise, for a manually-operated instrument, insertion may occur via movement of the entire instrument including the transmission assembly, via a user generally holding the instrument at least in part by the transmission assembly housing.

However, other instruments and manipulator systems provide for the insertion degree of freedom of the instrument shaft and end effector via drive input from the transmission assembly itself, thereby causing relative translation between the transmission assembly of the instrument and the shaft of the instrument. In such systems, the relative translation between the instrument shaft and the transmission assembly causes translation of the instrument shaft, with the end effector coupled to the shaft, relative to the workspace because the transmission assembly is held translationally stationary relative to the workspace by the manipulator to which the instrument is coupled.

The ability of the transmission assembly and instrument shaft to translate relative to each other results in a relatively complex architecture of drive and force transmission structures that make up the transmission assembly. There exists a need to provide instruments with transmission assemblies that the insertion degree of freedom movement of the instrument to be driven by the transmission assembly while still being relatively simple and compact in its overall architecture to provide the drive forces associated with the other functionality of the instrument, and/or to otherwise improve performance of instruments with such transmission assembly architectures.

SUMMARY

Various embodiments of the present disclosure may solve one or more of the above-mentioned problems and/or may demonstrate one or more of the above-mentioned desirable features. Other features and/or advantages may become apparent from the description that follows.

In accordance with at least one embodiment of the present disclosure, a medical instrument comprises an instrument shaft, a movable component coupled to the instrument shaft, a rotational actuation element extending through the instrument shaft and operably coupled to the movable component, and a transmission assembly movably coupled to the instrument shaft. The transmission assembly comprises a first drive member configured to drive translation of the instrument shaft relative to the transmission assembly, and a second drive member coupled to the rotational actuation element and configured to drive rotation of the rotational actuation element. Translation of the instrument shaft relative to the transmission assembly causes translation of the rotational actuation element relative to the transmission assembly.

In accordance with at least one embodiment of the present disclosure, a method of operating a medical instrument is provided. The medical instrument comprises an instrument shaft, a transmission assembly, and a movable component. The method comprises causing motion of the instrument shaft relative to the transmission assembly by driving a first drive member of the transmission assembly, and causing motion of the movable component by driving a second drive member of the transmission assembly to rotate a rotational actuation element operably coupled to the movable component. Translation of the instrument shaft relative to the transmission assembly causes translation of the rotational actuation element relative to the transmission assembly.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings.

DETAILED DESCRIPTION

Figure 1A:
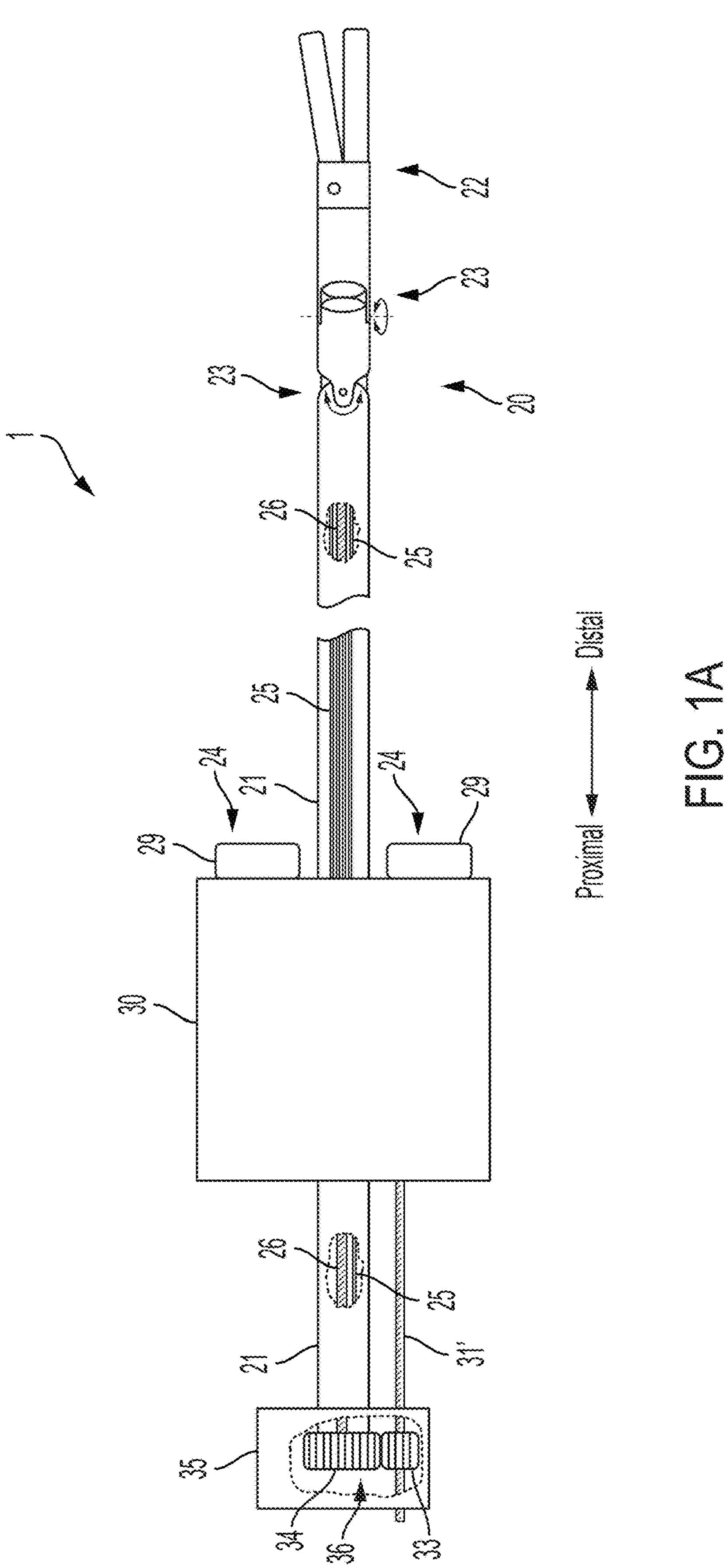
FIG. 1A is a schematic diagram of an embodiment of an instrument.

In the description below, reference is made to pullable actuation elements, pushable actuation elements, and rotational actuation elements. Pullable actuation elements refer to actuation elements that comprise flexible pulling members (such as cables, wires, filaments, belts, chains, straps, ropes, etc.) configured to transfer pulling (tensioning) forces while also being relatively flexible in directions perpendicular to a longitudinal dimension of the member. Pushable actuation elements refer to actuation elements that comprise members configured to transfer pushing (compression) forces, including rigid members that are capable of transmitting both pushing and pulling forces (such as rigid tubes, rods, bars, beams, etc.) and semi-flexible members that are capable of transmitting axial pushing forces (and in some cases also pulling forces) but which are flexible in one or more lateral directions (such as push coils, cut tubes, laterally supported cables (e.g., so-called "push-cables"), thin beams or plates that are flexible along one lateral dimension, etc.), or any combination of these. Use of the term "pushable" should not be misconstrued as implying that the pushable actuation elements cannot also transfer pulling forces, as some pushable actuation elements may be capable of doing so (sometimes called push-pull members). Rotational actuation elements refer to actuation elements configured to transfer rotary motion and torque (forces urging rotary motion), such as torque tubes, screws, bars, shafts, flexible coiled wire rotary tubes, etc. In some cases, similar types of members could be used as either rotational actuation elements or as pushable actuation elements, depending on how the member is driven.

In the description below, reference is also made to "paying out" or "drawing in" pullable actuation elements. Paying out a pullable actuation element refers to increasing the length of a segment of the actuation element that extends between a take-off point on a drive member to which the actuation element is coupled and a coupling point at which the actuation element is operably coupled to a moveable component whose motions are driven by the actuation element. Conversely, drawing in the pullable actuation element refers to decreasing the length of the segment of the actuation element that extends between the take-off point of the drive member and the coupling point of the driven moveable component. By extension, "paid-out length" refers to the current length of the above-described segment of the actuation element that extends between the take-off point and the coupling point. Furthermore, in the description below, reference is made to the "path length" for a pullable actuation element. The path length refers to the length of a hypothetical path that the above-described segment would be expected to traverse as it extends between the take-off point and the coupling point, assuming that the segment has no slack. The path length does not necessarily always equal the paid-out length, as some slack may be present resulting in the paid-out length exceeding the path length. References to "actuating" a pullable actuation element refer to causing the pullable actuation element to be paid out or drawn in, while references to "actuating" a pushable actuation element refer to causing the pushable actuation element to translate relative to some reference point such as the instrument shaft. References to "actuating" a drive member refer to causing the drive member to move (e.g., rotate) so as to perform some action, such as actuating an actuation element coupled thereto. The above-described terms and definitions are explained in further detail below, in and following the description of the various embodiments.

As noted above, in instruments for which an insertion degree of freedom occurs by a drive input at a transmission assembly of the instrument causing relative translation between the transmission assembly and the instrument shaft, the transmission assembly can result in a complex architecture. Some aspects of one embodiment of such a transmission assembly are described briefly below to illustrate some of the challenges that may arise in such instruments. In an embodiment of a transmission assembly, one of the drive members, also referred to hereinafter as the insertion drive member, drives translation of the instrument shaft relative to the transmission assembly to achieve the insertion degree of freedom motion of the instrument shaft and end effector. Various other drive members of such a transmission assembly, also referred to hereinafter as non-insertion drive members, can each be coupled to at least one respectively corresponding actuation element in the form of pullable actuation elements that are actuated (drawn in or paid out) to drive a degree of freedom of motion (or other function) of the instrument. The insertion drive member may comprise a drum to which multiple pullable actuation elements are coupled. The actuation elements coupled to the drum include one actuation element coupled to a proximal portion of the instrument shaft to drive relative translation of the shaft and transmission assembly in one direction, and also at least some of the actuation elements that are coupled to the non-insertion drive members (in some cases, all of the actuation elements that are coupled to the non-insertion drive members). The insertion drive member and the non-insertion drive members are configured such that rotation of the insertion drive member actuates (pays out or draws in) all of the actuation elements coupled thereto independently of rotation of the non-insertion drive members, thereby causing relative translation between the shaft and transmission assembly but without consequent actuation of the movable components (e.g., end effector, wrist, etc.) coupled to the non-insertion drive members. Individual actuation elements coupled to the non-insertion drive members can also be actuated independently of the insertion drive member to cause actuation of a movable component by rotation of a corresponding one of the non-insertion drive members. In such a transmission assembly, there can be numerous actuation element segments extending between the insertion drive member and the non-insertion drive members as well as segments extending between the various drive members and the instrument shaft. It can be challenging to arrange the drive members and the actuation elements of the transmission assembly in an orderly manner that allows the cables and drive members to function as intended without tangling or otherwise interfering with one another. This can be particularly challenging when trying to design a more compact transmission assembly or when trying to include a large number of drive members, actuation elements, or other components in the transmission assembly, as generally speaking the smaller the transmission assembly is, or the more drive members or other components are included therein, the more likely it is that an interference may occur with the actuation elements routed through the transmission assembly.

Another challenge for instruments in which the transmission assembly drives the insertion degree of freedom pertains to how to transmit pushing forces to the end effector or other movable components. In some instrument architectures, pushing forces may be transmitted to the end effector using pushable actuation elements, such as rods, tubes, push-coils, and the like or using rotational actuation elements coupled with a rotary-to-linear conversion mechanism, such as a lead screw coupled with a follower nut. However, because the transmission assembly moves relative to the shaft, it may be challenging to couple such pushable or rotational actuation elements to the drive inputs of the transmission assembly because the motion of the transmission assembly relative to the shaft may result in corresponding motion of the actuation elements relative to the shaft, which can cause inadvertent actuation of the movable element that is driven by actuation element.

Moreover, some types of end effectors, such as some staplers for example, may need relatively large pushing forces to drive some degrees of freedom of motion, such as a degree of freedom associated with jaw closing and/or staple firing. In some embodiments, pushing forces on the order of 50 pounds, 100 pounds, or even greater driving forces may be needed. In addition, in some types of end effectors, such as some staplers for example, the aforementioned pushing forces may need to be delivered over relatively long range of motion, such as a range of motion on the order of an inch, two inches, or even longer. However, it may be difficult to provide a relatively compact transmission assembly that can translate relative to the instrument shaft while also being able to adequately supply such large driving forces and/or such long driving distances to the pushable actuation element.

To address some of the issues noted above and otherwise improve remotely controlled instruments, some embodiments disclosed herein comprise a rotational actuation element that is coupled to and actuatable by a drive member of the transmission assembly to drive a degree of freedom of motion of a movable component, with the rotational actuation element being configured to float relative to the transmission assembly such that relative translation between the transmission assembly and the instrument shaft does not affect a position of the rotational actuation element relative to the instrument shaft. In other words, the rotational actuation element is configured to follow (remain stationary relative to) the instrument shaft such that both the rotational actuation element and the instrument shaft translate together relative to the transmission assembly when the insertion degree of freedom of motion is actuated. This floating of the rotational actuation element relative to the transmission assembly may be enabled by a gear assembly and a drive shaft that couple the rotational actuation element to the transmission assembly. In particular, the drive member that actuates the rotational actuation element comprises a drive shaft that extends proximally out of the transmission assembly to couple with a first gear of a gear assembly. This drive shaft may sometimes be referred to herein as an extended drive shaft, to differentiate it from the drive shafts of other drive members. The extended drive shaft is coupled to the first gear such that the extended drive shaft and the first gear are constrained to rotate together but can translate relative to one another along a longitudinal axis of the extended drive shaft. For example, a spline mechanism may be used to couple the extended drive shaft and first gear to one another. The rotational actuation element extends through the instrument shaft to couple with a second gear of the gear assembly such that the rotational actuation element is rotationally and translationally fixed relative to the second gear. The gear assembly is coupled to a proximal end portion of the instrument shaft such that the gear assembly is translationally fixed to the instrument shaft. Thus, the rotational actuation element, the instrument shaft, and the gear assembly are all translationally fixed relative to one another, but they can all translate together as a group relative to and along the extended drive shaft, and hence relative to the transmission assembly coupled to the extended drive shaft, by virtue of the translatable coupling between the first gear and the drive shaft. Moreover, the gears of the gear assembly are meshed together such that rotation of extended drive shaft drives rotation of the first gear, which drives rotation of the second gear, which drives rotation of the rotational actuation element. Thus, the drive member is able to actuate the rotational actuation element by rotating the extended drive shaft. This in turn allows the rotational actuation element to float relative to the transmission assemble while still being drivable by a drive member of the transmission assembly.

The rotational actuation element may be coupled with a rotatory-to-linear motion conversion mechanism that is coupled (directly or indirectly) with the movable component, such that the rotation of the rotational actuation element is converted into a pushing force that drives translation of the movable component. For example, in some embodiments, the rotational actuation element may comprise a lead screw and the rotary-to-linear conversion mechanism may comprise a follower nut engaged with the lead screw. Accordingly, the above-described configurations allow for pushing forces to be delivered to a movable component even in instruments with transmission assemblies that are movable relative to the instrument shaft, thereby expanding the functionalities of the instrument. Moreover, in some embodiments the transmission assembly may be capable of delivering relatively strong pushing forces (e.g., 50 pounds, 100 pounds, or even more) over a relatively long range of motion (e.g., over 1 inch, 2 inches, or even farther). For example, a lead screw and follower nut configuration, as used in some embodiments described herein, may provide a mechanical advantage that can allow for relatively strong pushing forces to be applied over a relatively long range of motion for a given amount of input torque. In some embodiments, such rotational actuation elements may be used, for example, in instruments comprising a stapler as an end effector, with the rotational actuation element driving a jaw closing and/or staple firing degree of freedom of motion.

Turning now to the figures, various embodiments will be described in greater detail. In the figures and in the description below, reference numerals are used to identify various parts, and in some cases in which multiple instances of the same or similar part are present, characters may be appended to the end of a base reference numeral to help to distinguish one particular instance of a part from another instance of the same or similar part. The appended characters may be omitted when the parts are being referred to generally without need to distinguish different instances of the same part. In particular, to identify different instances of the same or similar part the appended characters may take the form _N where N is any integer. For example, two drive members 400 may be referred to with the reference numbers 400_1 and 400_2 when desired to identify and differentiate specific drive members 400, or may be referred to generically by the reference number 400 when differentiation of specific instances is not desired. Moreover, the appended characters may also take the form of '(i.e., the apostrophe or prime character), to even further differentiate similar parts. For example, two actuation transfer mechanisms 430 of the same drive member 400_2 may be referred to with the reference numbers 430_2 and 430_2', with the _2 indicating that the two transfer mechanism 430 are associated with the drive member 400_2 and the ' differentiating these two transfer mechanisms 430 from one another. In addition, letters such as a, b, c, etc. may also be appended to a reference number to indicate different portions or aspects of a part. For example, distal and proximal portions of an instrument shaft 100 may be labeled as **100*a* and 100*b***, respectively.

FIGS. 1A-1D illustrate an embodiment of an instrument 1. FIGS. 2-11 illustrate various views of another embodiment of an instrument 10. The instrument 10 may be used as the instrument 1. In some embodiments, it is contemplated that either of the instruments 1 or 10 is used with and controlled via a computer-controlled teleoperated system, such as the system 1000 described below in relation to FIG. 17. For example, the instruments 1 or 10 may be used as the instrument 1002 in FIG. 17. While various embodiments described herein contemplate an instrument configured to be mounted to a manipulator system of a computer-controlled teleoperated system, those having ordinary skill in the art would appreciate that a manually-operated instrument is also contemplated, in which case various drive members can be configured to be operated via manual drive inputs, such as wheels, buttons, and the like.

In some embodiments, the instrument 1 or 10 is a medical instrument, which may be used to perform medical procedures, such as, for example, surgical, diagnostic, or therapeutic procedures. Medical instruments may include a variety of instruments used to perform medical procedures, such as therapeutic instruments, diagnostic instruments, surgical instruments, and/or imaging instruments. In some examples, the medical instruments may be inserted into a patient through a natural orifice or an incision (including through a port or other guide inserted in the incision). Such instruments that are remotely controlled may be particularly useful, for example, in performing minimally invasive surgical procedures. A minimally invasive medical procedure may be designed to reduce the amount of trauma to tissue during the procedure, for example by decreasing the number and/or size of incisions through which medical instruments are inserted. In other embodiments, the instrument 1 or 10 may be a non-medical instrument, such as an industrial instrument used for remote inspection or other remote procedures.

Overview of Embodiments of Instruments

As shown in FIG. 1A, an embodiment of an instrument 1 comprises a shaft 21 having a distal end portion supporting an end effector 22 and one or more other movable components 20 at the distal end portion of the shaft 21 (proximal and distal directions referenced herein are illustrated in FIG. 1A). The end effector 22 is configured to perform one or more functions. The one or more movable components 20 may comprise one or more components of the end effector 22 that are drivable to move (e.g., a jaw member, a translating staple firing component, etc.) and/or one or more articulable structures 23, such as joints. The instrument 1 also comprises a force transmission assembly 30, which is movably coupled to the shaft 21 proximal of the movable components 20 (the shaft 21 and force transmission assembly 30 move relative to one another, as described below, and thus the coupling location of the transmission assembly 30 to the shaft 21 varies, but the transmission assembly 30 remains positioned generally proximal of the movable component(s) 20 of the instrument 1). In various embodiments, the force transmission assembly is mountable to a manipulator of a computer-controlled, teleoperated system (such as the system 1000 described in further detail below), and input driving forces are provided to the instrument through the manipulator interface (as also describe in further detail below).

The end effector 22 is illustrated as having a jaw mechanism in FIG. 1A, but it should be understood that any other type of end effector could be used. Some non-limiting examples of end effectors 22 include staplers, forceps, vessel sealers, imaging devices (e.g., an endoscope tip), sensing devices (pressure, temperature, etc.), scissors, electrosurgical devices (e.g., monopolar or bipolar electrosurgical devices), other flux delivery devices (irrigation, suction, etc.), and so on. Functions performed by end effector 22 may include, for example, grasping, cutting, stapling, electrosurgical functions, illuminating, image capture, fluid delivery and/or evacuation, etc., as would be familiar to those of ordinary skill in the art. In some embodiments, one or more functions of the end effector 22 may involve motion of a movable component that is mechanically driven. In some embodiments, some functions of the end effector 22 may be driven non-mechanically, for example, by supplying electrical power or other functional flows (e.g., vacuum suction, light, etc.) to the end effector 22. Some functions of the end effector 22 may involve a combination of mechanical and non-mechanical driving inputs, such as an electrosurgical function which may comprise a mechanically driven operation of closing of a jaw member to grasp an object and an electrically driven operation of sealing or cutting the grasped object. In some embodiments, the end effector 22 does not necessarily comprise any movable components that are mechanically driven—by way of nonlimiting example, the end effector 22 may comprise an endoscope tip with an imaging device or a monopolar electrosurgical tip member.

As shown in FIG. 1A, the force transmission assembly 30 comprises drive members 24 configured to receive input driving forces via drive inputs 29, with the driving forces controlling degrees of freedom of motion of the instrument 1. The drive members 24 convert and transfer the driving forces to actuation elements 25 and 26, such as flexible pullable actuation elements 25 (e.g., cables, wires, filaments, etc.) and rotational actuation elements 26 (e.g., lead screw, shaft, etc.) to drive motion of the end effector 22 and/or movable components 20 or other parts of the instrument 1. Although not shown in FIG. 1A, the instrument may also comprise pushable actuation elements (e.g., beams, rods, tubes, push-coils, etc.), which may include pushable members to control degrees of freedom of motion. The flexible pullable actuation elements 25 may also be referred to herein as "pullable actuation elements 25," or "actuation elements 25". The rotational actuation elements 26 may also be referred to herein as "actuation elements 26". The pullable actuation elements 25 and the rotational actuation elements 26 may be coupled to and driven by corresponding drive members 24. As shown in FIG. 1A, the pullable actuation elements 25 may extend distally and proximally from the force transmission assembly 30 through and/or along the shaft 21 and may be coupled to various parts of the instrument 1 to drive degrees of freedom of motion, such as to one of the movable components 20, another actuation element (e.g., a pushable actuation element), or the instrument shaft 21. In some embodiments, the pullable actuation elements 25 may pass along an exterior of the shaft 21 for a portion thereof and then may pass through an interior of the shaft 21 along another portion thereof, as illustrated in FIG. 1A. The rotational actuation element 26 also extends through at least a portion of the instrument shaft 21, and is coupled (directly or indirectly) with one of movable components 20 to drive a degree of freedom of motion thereof.

Figures 1B, 1C, 1D:
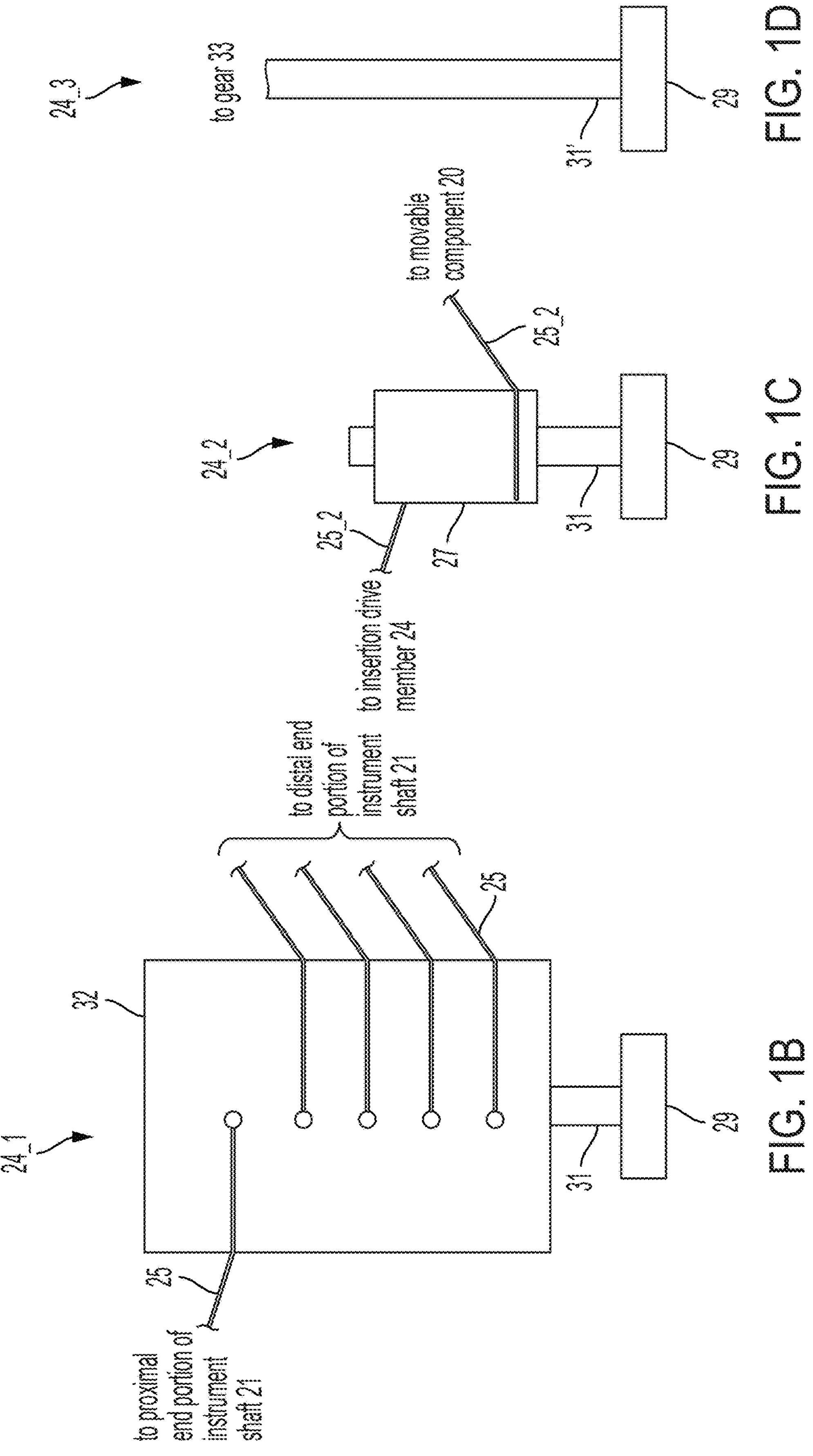
FIG. 1B is a schematic diagram of a drive member of the instrument of FIG. 1A.
FIG. 1C is a schematic diagram of another drive member of the instrument of FIG. 1A.
FIG. 1D is a schematic diagram of yet another drive member of the instrument of FIG. 1A.

One of the drive members 24 (also referred to as insertion drive member 24) is configured to drive an insertion degree of freedom of motion of the instrument (i.e., relative translation between the instrument shaft 21 and the force transmission assembly 30) by actuating two or more of the actuation elements 25. In particular, at least one of the proximally extending actuation elements 25 is coupled with the insertion drive member 24 and a proximal portion of the shaft 21 such that the insertion drive member 24 can drive translation of the shaft 21 in a distal direction relative to the transmission assembly 30 by drawing in this proximally coupled actuation element 25. In addition, at least one of the distally extending actuation elements 25 is coupled with the insertion drive member 24 and with a portion of the instrument that is distal of the force transmission assembly 30, such as a movable component 20, such that the insertion drive member 24 can drive translation of the shaft 21 in a proximal direction relative to the transmission assembly 30 by drawing in these distally coupled actuation elements 25. When the force transmission assembly 30 is in a fixed position relative to a workspace, such as mounted to a manipulator or otherwise held in a fixed position relative to a workspace, the above-noted relative translation results in translation of the shaft 21 relative to the fixed position at which the force transmission assembly 30 is coupled, which can be used for insertion or withdrawal of the end effector 22 relative to the workspace. As shown in FIG. 1B, in some embodiments the insertion drive member 24_1 comprises a drum 32 around which actuation elements 25 are at least partially wound, such that rotation of the insertion drive member 24_1 actuates the actuation elements 25. The drum 32 is coupled to one of the drive inputs 29, for example by a drive shaft 31. As shown in FIG. 1B, the pullable actuation elements 25 that are coupled to a distal end portion for the instrument shaft 21 (directly or via other components that are coupled to the instrument shaft 21) are wrapped around the drum 32 of the insertion drive member 24_1 in an opposite direction than the pullable actuation elements 25 that are coupled to the proximal end portion of the instrument shaft 21 (directly or via other components that are coupled to the instrument shaft 21), and therefore rotation of the drum 32 in one direction pays out the latter while simultaneously drawing in the former, and vice versa. In FIG. 1B, four pullable actuation elements 25 are shown that extend to the distal end portion of the instrument shaft 21 and one pullable actuation element 25 is shown that extends to the proximal end portion of the instrument shaft 21, but these are non-limiting examples and any number of pullable actuation elements 25 may be used as long as at least one pullable actuation element 25 is coupled to the distal end portion of the instrument shaft 21 and at least one is coupled to the proximal end portion of the instrument shaft 21.

As shown in FIG. 1C, one or more other drive members 24 are configured to drive additional degrees of freedom of motion by actuating one or more respectively corresponding actuation elements 25 coupled thereto. In particular, the non-insertion drive member 24_2 may actuate the pullable actuation element 25 to drive motion of one of the movable components 20, such as an articulable structure 23. As shown in FIG. 1C the non-insertion drive member 24_2 comprises a drive shaft 31 coupled to at least one actuation element handling device 27. The actuation element handling device 27 is coupled to a corresponding actuation element 25 such that rotation of the drive shaft 31 actuates (draws in or pays out) the corresponding actuation element 25. A drive input 29 is coupled to the drive shaft 31 to drive rotation thereof. The drive input 29 may receive input driving forces, for example which may be received from a manipulator or from manual input. Although only actuation element handling device 27 is illustrated in FIG. 1C, it should be understood that in some embodiments multiple actuation element handling devices 27 can be provided for a given drive member 24_2, allowing a single drive member 24_2 to actuate multiple actuation elements 25 simultaneously. In some embodiments, the actuation element handling devices 27 may be configured as actuation transfer devices, which are configured to allow an actuation element 25 coupled thereto to pass through the actuation element handling device 27 to also couple with the insertion drive member 24 such that the actuation element 25 can be independently actuated by both the insertion drive member 24 and the non-insertion drive member 24 of which the actuation element handling device 27 is a part. Thus, in some embodiments the actuation element 25_2 is coupled to and independently actuatable by both the insertion drive member 24_1 and the non-insertion drive member 24_2. The transmission assembly 30 may include any number of such drive members 24_2. The transmission assembly 30 may also include other drive members or other functionality, as would be understood to those of ordinary skill in the art.

In addition to the drive members 24 described above, the transmission assembly 30 also includes a drive member 24_3, as shown in FIG. 1D. Like the other drive members 24_1 and 24_2, the drive member 24_3 comprises a drive input 29 and drive shaft 31', but the drive shaft 31' of the drive member 24 may differ from the other drive shafts 31 in that it extends distally outside of the transmission assembly 30 to couple with a proximal gear housing 35 that is coupled to a proximal end portion of the instrument shaft 21. Thus, the drive shaft 31' may also be referred to herein as an extended drive shaft 31'. In addition, the extended drive shaft 31' is coupled to the gear 33 in the gear housing 35 and is configured to allow the gear 33 to translate relative to and along the drive shaft 31' while also constraining the gear 33 to rotate with the drive shaft 33'.

For example, the extended drive shaft 31' may comprise one or more anti-rotation features, such as splines (grooves or protrusions extending along longitudinal dimension of the drive shaft 31'), that engage (directly or via an intermediary) with complementary anti-rotation features on the gear 33. The anti-rotation features are configured such that they constrain the gear 33 to rotate with the drive shaft 31' while also allowing axial (longitudinal) translation of the gear 33 relative to the drive shaft 31'. For example, the anti-rotation features may extend in a longitudinal direction, thereby allowing relative axial translation but preventing relative rotation. In some embodiments, a spline mechanism, such as a ball spline mechanism or recirculating ball spline mechanism, may be used to couple the gear 33 to the extended drive shaft 31'. For example, such a ball spline mechanism may comprise a collection of ball bearings captured between the gear 33 and the extended drive shaft 31' such that one side of the ball bearing is engaged with an anti-rotation feature (e.g. groove) of the drive shaft 31' and the other side is engaged with an anti-rotation feature (e.g., a groove) of the gear 33. Thus, the ball bearings can roll in the axial direction along the anti-rotation features, allowing the gear 33 to translate relative to the extended drive shaft 31 with relatively low friction. However, the anti-rotation features (e.g., grooves) constrain the ball bearings and prevent them from moving in directions other than the axial direction, and therefore the gear 33 is constrained by the ball bearings and the anti-rotation features to be rotationally stationary relative to the extended drive shaft 31'. Ball spline mechanisms such as those described above are merely one way to couple the extended drive shaft 31' to the gear 33 while allowing axial translation of the gear 33 along the drive shaft 31', and it should be understood that in other embodiments different mechanisms could be used. For example, in some embodiments a plain bearing is used, i.e., the gear 33 engages directly with the extended drive shaft 31' without an intermediary. For example, the extended drive shaft 31' may have a groove in its outer surface that extends along the axial direction and the gear 33 may have a complementary protrusion that protrudes from an inwardly facing surface of the gear 33, with the groove and protrusion engaged with one another so as to prevent relative rotation between the gear 33 and the shaft 31' while allowing relative translation in the axial direction. (The reverse configuration could also be used, with the extended drive shaft 31' having a ridge extending in the axial direction and the gear having a groove in its inwardly facing surface). Any other type of coupling between the extended drive shaft 31' and the gear 33 that allows for relative axial translation while preventing relative rotation could also be used, as would be apparent to one of ordinary skill in the art.

Returning to FIG. 1A, the actuation of the rotational actuation element 26 via the drive member 24_3 will now be described. As shown in FIG. 1A, a proximal gear housing 35 is coupled to the proximal end portion of the instrument shaft 21. The proximal gear housing 35 comprises a gear assembly 36 comprising at least two gears, including the first gear 33 and second gear 34. Although only two gears are shown in FIG. 1A, additional gears may be used in the gear assembly 36 (any number of gears equal or greater than two), with the various additional gears being coupled together between the first and second gears 33 and 34 such that rotation of the first gear 33 drives rotation of the second gear 34. As shown in FIG. 1A and as noted above, the extended drive shaft 31' is coupled with the gear 33. Moreover, as shown in FIG. 1A, the gear 34 is coupled with the proximal end portion of the rotational actuation element 26 such that the rotational actuation element 26 is constrained to rotate with the gear 34. Thus, when the extended drive shaft 31' is rotated by the drive member 24_3, this causes the gears 33 and 34 to rotate, which causes the rotational actuation element 26 to rotate. Thus, the drive member 24_3 can actuate (i.e., rotate) the rotational actuation element 26.

Furthermore, when the insertion degree of freedom of motion is actuated by the drive member 24_1 such that the shaft 21 translates relative to the transmission assembly 30, the rotational actuation element 26 translates along with the instrument shaft 21 relative to the transmission assembly 30, thus preventing unintentional actuation of the movable component 20 to which the rotational actuation element 26 is coupled. The translation of the shaft 21 relative to the transmission assembly 30 urges the rotational actuation element 26 and the gear assembly 36 (including the gears 33 and 34) to also translate along with the instrument shaft 21, because the rotational actuation element 26 and the gear assembly 36 are translationally fixed relative to the instrument shaft 21. Although the extended drive shaft 31' is translationally fixed relative to the transmission assembly 30, this does not prevent the gear assembly 36 or rotational actuation element 26 from translating along with the instrument shaft 21 relative to the drive shaft 31' and the transmission assembly 30 because the gear 33 is coupled with the drive shaft 31' in a manner that allows for relative translation of the gear 33 along the drive shaft 31'. Thus, when the insertion degree of freedom of motion is actuated, the instrument shaft 21, rotational actuation element 26, and gear assembly 36 all translate together as a group relative to the transmission assembly 30 and the extended drive shaft 31'.

As noted above, the rotational actuation element 26 is coupled, directly or indirectly, with one of the movable components 20 to drive a degree of freedom of motion thereof. In some embodiments, the rotational actuation element 26 may be coupled with a rotatory-to-linear motion conversion mechanism (not illustrated) that is coupled (directly or indirectly) with the movable component 20, such that the rotation of the rotational actuation element 26 is converted into translational motion that generates a pushing and/or pulling force that drives motion of the movable component 20. In other embodiments, the desired output motion may be rotational, and thus the rotatory-to-linear motion conversion mechanism may be omitted and the rotational actuation element 26 may be coupled (directly or indirectly) to the movable component 20 to provide rotary motion and torque to the movable component 20.

In some embodiments in which the rotary-to-linear conversion mechanism is provided, the rotational actuation element 26 may comprise a lead screw and the rotary-to-linear conversion mechanism may comprise a follower nut engaged with the lead screw. The follower nut may be coupled to, or may be part of, the movable component 20, such that rotation of the rotatory actuation element 26 is converted into translation of the follower nut and translation of the follower nut drives the motion of the movable component. For example, in some embodiments, the follower nut is coupled to, or is part of, a translating component of an end effector 22, such as a staple firing shuttle of a stapler in some embodiments. The rotary-to-linear conversion mechanism may be coupled to the movable component 20, for example, by a pushable actuation element (not illustrated), such as a tube, bar, beam, coil pipe, cut tube, etc. Accordingly, the above-described configurations allow for pushing forces to be delivered to a movable component even in instruments with relative translation between the transmission assembly and the instrument shaft, thereby expanding the functionalities of the instrument. Moreover, in some embodiments the transmission assembly 30 may be capable of delivering relatively strong pushing forces over a relatively long range of motion. In some embodiments, rotational actuation element 26 may be configured to supply relatively strong translational pushing forces to one of the movable components 20, including pushing forces of at least 50 pounds (222 N) in some embodiments and at least 100 pounds (445 N) in some embodiments. Moreover, in some embodiments, the rotational actuation element 26 may be configured to allow a relatively long range of motion for the movable component 20 driven thereby, including a range of motion of at least one inch (2.5 cm) in some embodiments and at least 2 inches (5.1 cm) in some embodiments.

Returning to FIG. 1A, in some embodiments the one or more movable components 20 of the instrument 1 include one or more articulable structures 23 (such as jointed links, a wrist mechanism, flexible/bendable portions of a shaft, such as via laser cut or other reliefs, etc.). Each articulable structure 23 has at least one corresponding degree of freedom of motion, which is driven by one or more actuation elements 25 coupled to the articulable structure 23. The articulable structure 23 can be used to couple the end effector 22 to the shaft 21 to allow for relative motion between the end effector 22 (or some other component) and the shaft 21, thereby allowing the pose of the end effector 22 to be changed. Such placement for an articulable structure 23 is nonlimiting and articulable structures 23 can be used along the instrument shaft 21 to provide differing poses of portions of the shaft relative to other portions of the shaft 21, as those having ordinary skill in the art would be familiar with. In some embodiments, the articulable structure 23 provides differing degrees of freedom of motion. In some embodiments, multiple articulable structures 23 having differing degrees of freedom of motion are connected in series to form a wrist mechanism that couples the end effector 22 to the shaft 21 and to enable the end effector 22 to move with two or more degrees of freedom of motion (e.g., yaw, pitch, or combinations thereof) relative to the shaft 21. In some embodiments, the end effector 22 is coupled directly to the shaft 21 without an intervening articulable structure 23. References herein to an end effector being coupled to or supported by a shaft should be understood as broadly including both direct coupling and indirect coupling (e.g., via an articulable structure 230 or other intervening component), unless otherwise indicated or implied by the context. Although two articulable structures 23 comprising rotating joints are illustrated in FIG. 1A, it should be understood that this is not limiting and any number or type of articulable structure 23 could be used instead, including zero, one, three, or more articulable structures 23.

Moreover, in some embodiments, the one or more movable components 20 of the instrument 1 comprise movable components of the end effector 22 (in addition to, or in lieu of the articulable structures 23). In such embodiments, the movable components of the end effector 22 may be mechanically driven by driving forces transmitted to the end effector 22 from the drive members 24 via the rotational actuation element 26, as already described above and/or by flexible pullable actuation elements 25 and/or by other actuation elements (not illustrated) such as pushable actuation elements. Examples of such movable components of an end effector 22 may include a translatable staple firing component, a pivotable jaw member of a jaw mechanism, a translatable cutting element, etc. Such movable components of the end effector 22, when present, are instances of the above-noted movable components 20, and their motion may be considered a degree of freedom of motion of the instrument 1.

In particular, in some embodiments the end effector 22 comprises a stapler, which comprises a translatable staple firing component. In some embodiments the rotational actuation element 26 drives the translatable staple firing component. In some embodiments, initial translation of the translatable staple firing component in a distal direction may cause a jaw mechanism of the stapler to close. In addition, further translation of the translatable staple firing component in the distal direction may fire staples from the jaw mechanism into a material by the jaw mechanism as a result of the staple firing component colliding with and pushing the staples out of the jaw mechanism. The closing of the jaw mechanisms may require relatively large driving forces due to possible resistance of the grasped material to being compressed between jaw members of the stapler. Similarly, the firing of the staples may require relatively large driving forces, due to friction and other forms of resistance such as resistance of the staples to being deformed and resistance of the grasped material to being pierced. However, in some embodiments, the rotational actuation element 26 and the drive member 24 that drives it are configured to be able to provide sufficiently strong driving forces to actuate such a translatable staple firing component.

The instrument 1 may also have additional degrees of freedom of motion. For example, in some embodiments the shaft 21 may be rotatable about its longitudinal axis, relative to the workspace, by rotation of the entire instrument 1 about the longitudinal axis. This may occur, for example, by rotation of an instrument holder to which the instrument 10 is mounted relative to a support that the instrument holder is coupled with (and hence rotation of the instrument 1 as a whole relative to the support). Such rotation of the instrument shaft 21 may be referred to as a roll degree of freedom of motion.

Although FIGS. 1A-1D illustrate an embodiment having both drive members 24_2 of the type illustrated in FIG. 1C and drive members 24_3 of the type illustrated in FIG. 1D, it should be understood that embodiments with different combinations of these parts are contemplated herein. In particular, embodiments contemplated herein include at least embodiments that have both one or more drive members 24_2 and one or more drive members 24_3, embodiments that have one or more drive members 24_2 but no drive members 24_3, and embodiments that have one or more drive members 24_3 but no drive members 24_2. Embodiments contemplated herein may also include additional types of drive members besides those illustrated in FIGS. 1A-1D. Other combinations of the various components are also contemplated herein, as would be apparent to a person of ordinary skill in the art.

Turning now to FIGS. 2-9, another embodiment of an instrument 10 is described below. The instrument 10 may be used as the instrument 1. The descriptions above of parts of the instrument 1 are applicable mutatis mutandis to the similar parts of the instrument 10.

Figure 2:
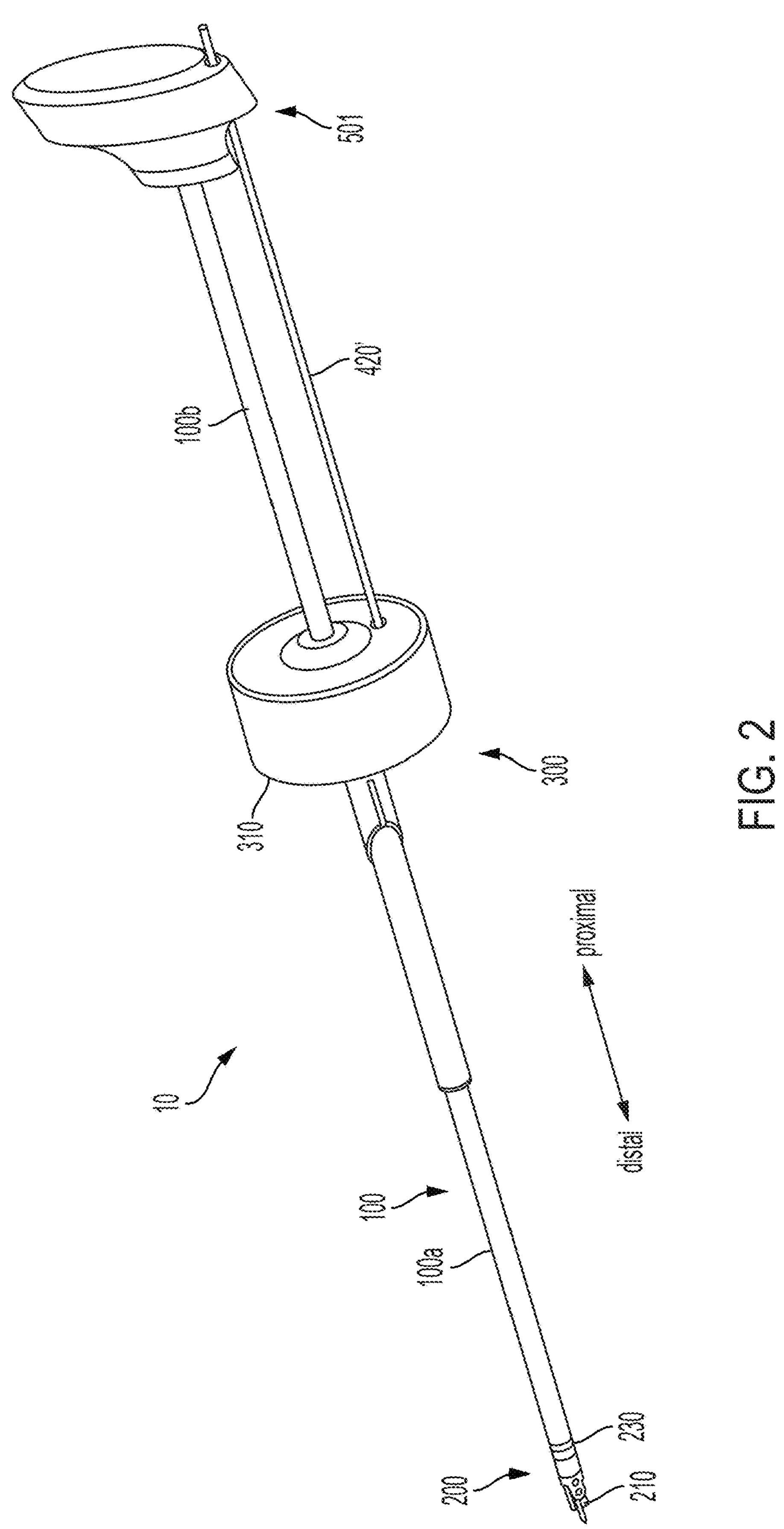
FIG. 2 is a perspective view of another embodiment of an instrument.

As shown in FIG. 2, an embodiment of an instrument 10 comprises a shaft 100 supporting an end effector 210 at a distal end portion of the shaft 100 (proximal and distal directions referenced herein are illustrated in FIG. 2). The end effector 210 is configured to perform one or more functions, similar to the end effector 22 as described above. The instrument 10 also comprises one or more movable components 200, similar to the movable components 20 described above, coupled to a distal end portion of the shaft 100. The one or more movable components 200 may comprise one or more components of the end effector 210 (e.g., a jaw member of a jaw assembly, a translating component such as a cutting component, etc.) and/or one or more articulable structures 230 coupling the end effector 210 (or some other component of the instrument 10) to the shaft 100 and/or provided along the shaft 100 to impart articulation to the shaft 100. The instrument 10 also comprises a force transmission assembly 300, similar to the force transmission assembly 30 described above, which is movably coupled to the shaft 100 proximal of the movable components 200 (the shaft 100 and force transmission assembly 300 move relative to one another, as described below, and thus the coupling location of the transmission assembly 300 to the shaft 100 varies, but the transmission assembly 300 remains positioned generally proximal of the movable component(s) 200 of the instrument 10). The instrument also comprises a gear housing 501 coupled to the proximal end portion **100*b* of the shaft 100**.

Figure 4:
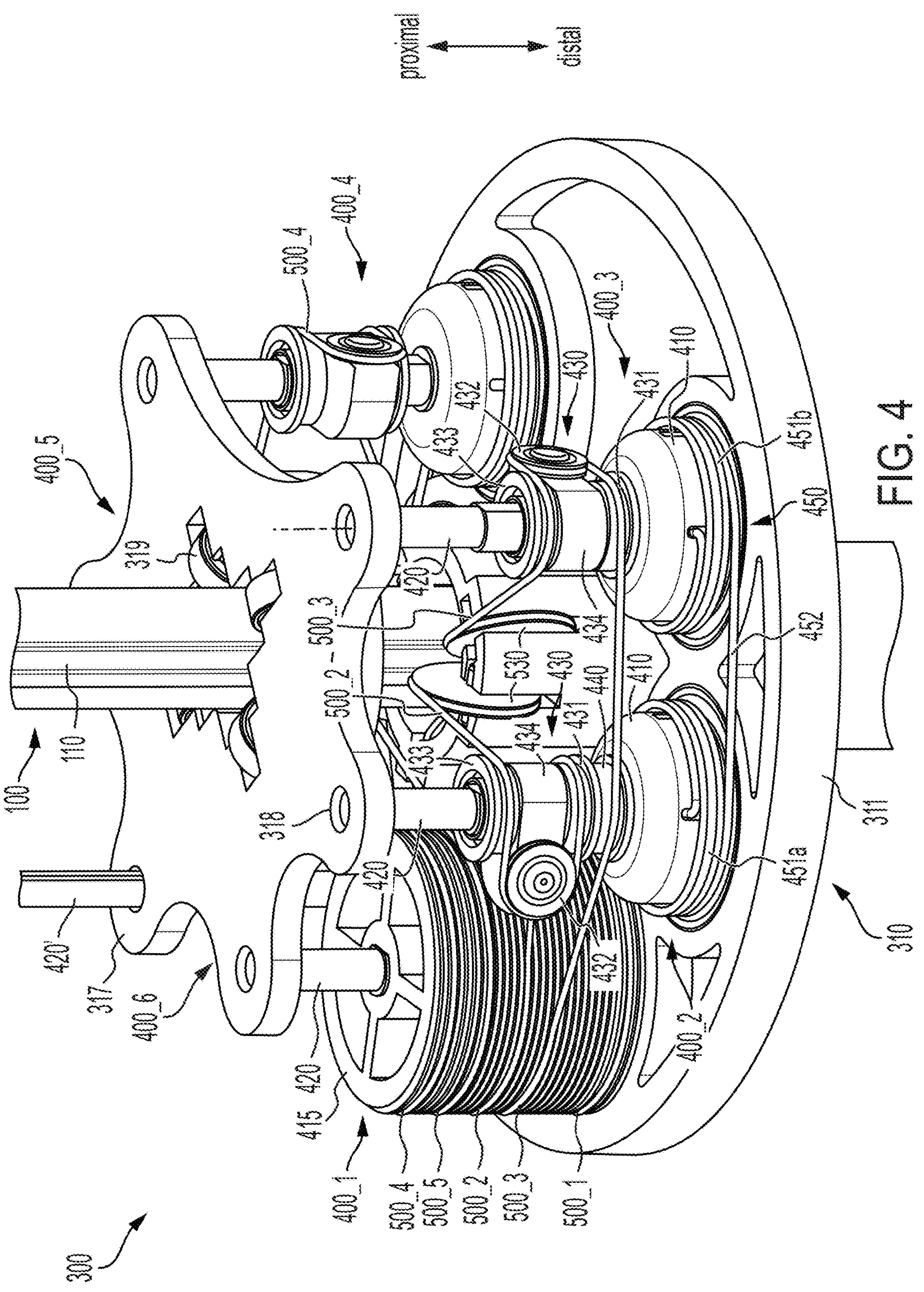
FIG. 4 is a perspective view of an embodiment of a transmission assembly of the instrument of FIG. 2 with a cover portion removed.

With further reference to FIG. 4, the force transmission assembly 300 may be used as the force transmission assembly 30 and comprises drive members 400 configured to receive input driving forces, with the driving forces controlling degrees of freedom of motion of the instrument 10. In various embodiments, the force transmission assembly 300 is mountable to a manipulator of a computer-controlled, teleoperated system (such as the system 1000 described in further detail below in connection with FIG. 17), and the input driving forces are provided to the drive members 400 through the manipulator interface (as also describe in further detail below in connection with FIG. 18). The drive members 400 may be used as the drive members 24 described above. The drive members 400 convert and transfer the driving forces to actuation elements, including flexible pullable actuation elements 500, and rotational actuation element 120. The flexible pullable actuation elements 500 may be used as the actuation elements 25 described above, and the rotational actuation element 120 may be used as the actuation element 26 described above.

The flexible pullable actuation elements 500 may also be referred to herein as "pullable actuation elements 500" or "actuation elements 500." The actuation elements 500 may comprise tension members capable of transmitting pulling (tensioning) forces while also being relatively flexible in lateral directions perpendicular to a longitudinal dimension of the member, such as, for example, cables, wires, filaments, belts, chains, straps, ropes, etc. Such pullable actuation elements may also be referred to as tension members or pull-pull actuation elements. The drive members 400_2 to 400_5 may be used as the drive member 24_2 described above, while the drive members 400_6 may be used as the drive member 24_3 described above.

The pullable actuation elements 500 extend through and/or along the shaft 100 and are coupled to the movable components 200 and/or other parts of the instrument 10 to transmit the driving forces so as to drive various degrees of freedom of motion of the instrument 10, which may include degrees of freedom of motion of the movable components 200 as well as additional degrees of freedom of motion. For example, some of the actuation elements 500 are coupled to and drive motions of articulable structures 230 (such as jointed links, flexible portions of a shaft, etc.), each of which has at least one corresponding degree of freedom of motion. Other actuation elements 500 may be coupled to the shaft 100, for example to drive an insertion degree of freedom of motion.

The rotational actuation element 120 may also be referred to herein as an "actuation element 120". The rotational actuation element 120 may comprise a member capable of transmitting torque (rotational forces). For example, the rotational actuation element 120 may comprise one or more shafts, lead screws, tubes, rods, bars, or the like. In some embodiments, the rotational actuation element 120 is coupled to a rotary-to-linear conversion mechanism to convert the rotation of the actuation element 120 into translational motion the movable component 200. In some embodiments, the rotary-to-linear conversion mechanism is part of the end effector 210 or other movable component 200 driven by the actuation element 120. In some embodiments, the rotary-to-linear conversion mechanism is used to couple the rotatory actuation element 120 to a translatable push member, with the push member being coupled to the to transmit translational drive forces to end effector 210 or other movable component 200.

In some embodiments that comprise articulable structures 230, it may be beneficial for actuation elements that extend through the articulable structure 230 to be laterally flexible, so that they can bend with the articulable structure 230 when the articulable structure 230 is articulated. Thus, in some embodiments the rotational actuation element 120 comprises a laterally flexible rotational member, such as a tubular cable structure comprising one or more layers of cables wound or coiled around a rotational axis to form a tube, a tub which has been cut repeatedly along a length thereof to impart lateral flexibility, or any other laterally flexible rotational member. Examples of tubular cable structures, including multi-layer tubular cable structures, are described in U.S. Pat. No. 9,055,961, the contents of which are incorporated herein by reference in their entirety. In some embodiments, the laterally flexible rotational member extends along all or substantially all of the length of the rotational actuation element 120; in other words, substantially all of the rotational actuation element 120 is laterally flexible. In other embodiments, the laterally flexible rotational member forms just a portion of the rotational actuation element 120, with one or more other portions of the rotational actuation element 120 comprising relatively rigid rotational members. In other words, in various embodiments the rotational actuation element 120 has a multi-part structure with one portion being relatively rigid and another portion joined thereto being relatively flexible in lateral directions. The rigid portions of the rotational actuation element 120 may comprise, for example, a rigid tube, bar, screw, shaft, or other rigid rotational member. The flexible portions of the rotational actuation element 120 may comprise any of the laterally flexible rotational members described above. The rigid and flexible portions may be joined together to rotate together, for example, by welding, mechanical fasteners (e.g., crimping), etc. In the above-described embodiments in which either all or a portion of the rotational actuation element 120 is laterally flexible, a flexible portion of rotational actuation element 120 may extend through the articulable structure 230. Thus, in some of these embodiments, the rotatory-to-linear conversion mechanism (if any) may be located distal of the articulable structure 230, such as at the end effector 210.

In other embodiments, the rotational element 120 does not comprise a flexible portion, and instead a separate flexible member is coupled to the rotational element 120. For example, as noted above, in some embodiments the rotational element 120 is coupled with a translatable push member via a rotatory-to-linear conversion mechanism, and in some of these embodiments the push member may be laterally flexible while the rotational element 120 is relatively more rigid. In such embodiments, the rotatory-to-linear conversion mechanism may be located proximal of the articulable structure 230 so that the more flexible push member can extend through the articulable structure 230. The laterally flexible push member may be relatively rigid axially and capable of transmitting pushing forces (and in some cases also pulling forces) while also being laterally flexible in multiple dimensions. Examples of such laterally flexible push members include a coil pipe, a cut tube (e.g., laser cut tubes), a flexible pullable member (e.g., cable) that is laterally surrounded by a supporting structure to prevent buckling when a pushing force is applied, or the like. In some embodiments, the flexible push member may have a multi-part structure, such as, for example, a structure comprising a push-coil and a cable with the cable extending through a central lumen of the push-coil.

Figure 5:
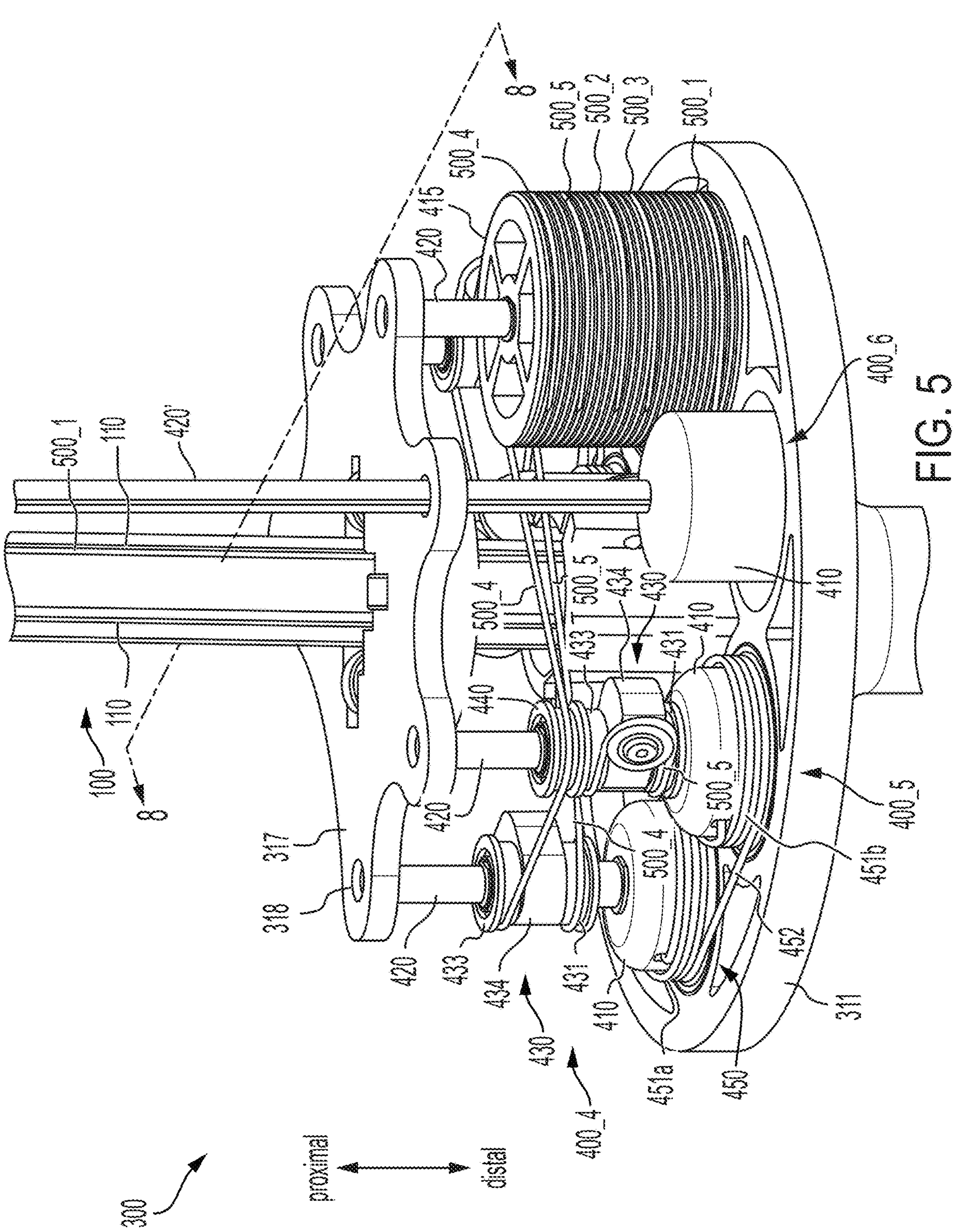
FIG. 5 is another perspective view of the transmission assembly of FIG. 4 with the housing cover portion removed.
Figure 6:
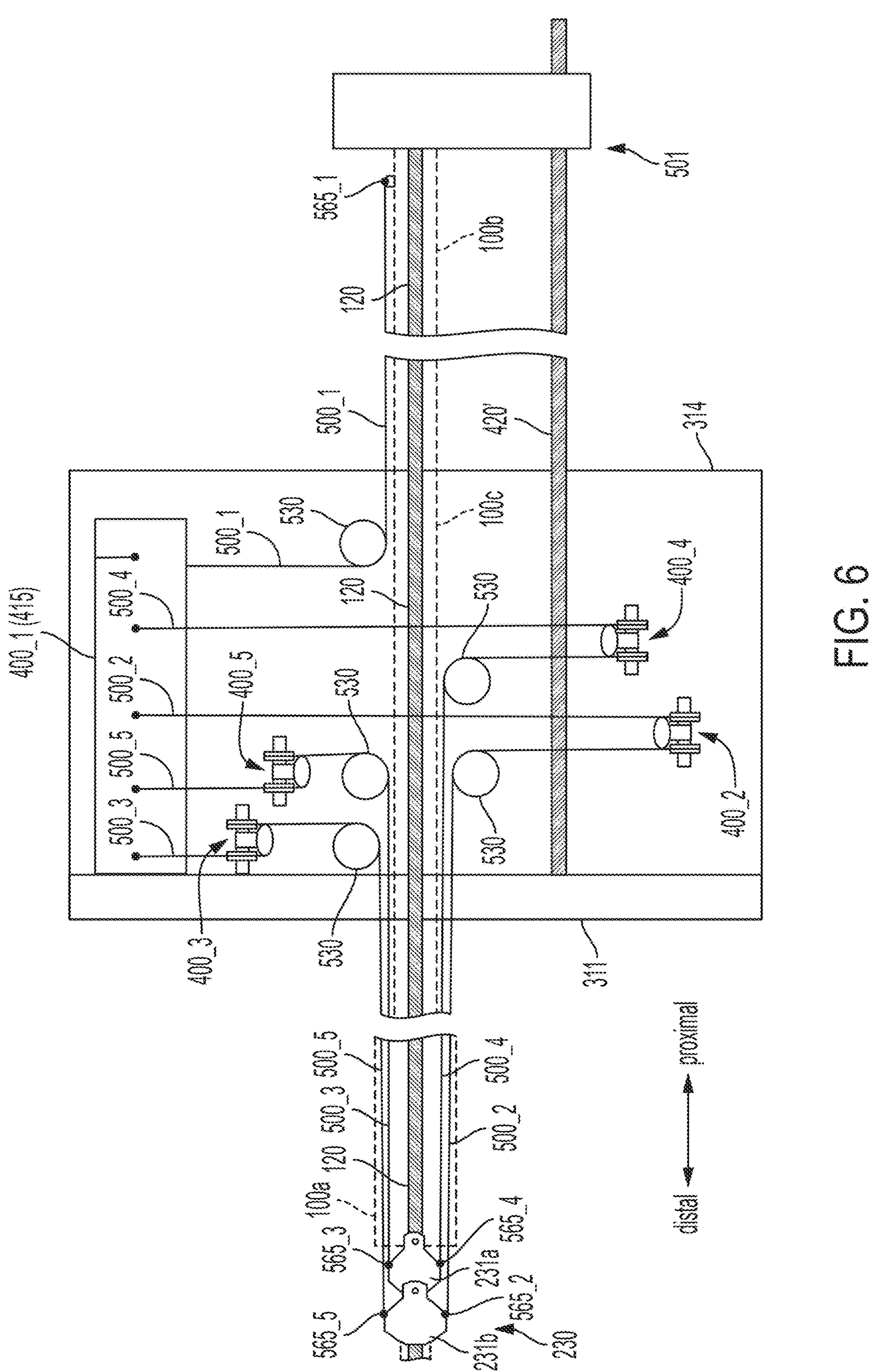
FIG. 6 is a schematic diagram of portions of the instrument of FIG. 2.

As noted above, some portions of the actuation elements 500 may be routed inside the instrument shaft 100 and other portions may be routed external to the instrument shaft 100. More specifically, as shown in FIGS. 5 and 6, in some embodiments the actuation elements 500 may be routed inside of the instrument shaft 100 while passing through a distal portion 100*a* of the instrument shaft 100 and the actuation elements 500 may be routed along an exterior of the instrument shaft 100 while traversing an intermediate portion 100*c* of the shaft 100, the intermediate portion 100*c* being located between the distal portion 100*a* and a proximal portions 100*b*. The actuation element 500 may be located either along the exterior or the interior of the shaft 100 while in the proximal portion 100*b* of the shaft 100. The intermediate portion 100*c* may comprise a portion of the instrument shaft 100 along which the transmission assembly 300 translates. In some embodiments, while passing along the exterior of the instrument shaft 100, the actuation elements 500 may be routed through grooves 110 in an exterior surface of the instrument shaft 100 (grooves 110 shown in FIGS. 4 and 5). The actuation elements 500 may transition from the exterior of the instrument shaft 100 to an interior thereof via openings (not illustrated) in and through an outer wall of the instrument shaft 100.

Paying out or drawing in one of the actuation elements 500 may also be referred to herein as "actuating" the actuation element 500 when the particular direction of motion (i.e., paying out or drawing in) is not specified. Similarly, rotation of the rotational actuation elements 120 may also be referred to herein generically as "actuating" the actuation element 120. In addition, causing a drive shaft 420 of a drive member 400 (described in detail below) to rotate may also be referred to herein as "actuating" the drive element 400. Thus, using this nomenclature, a given actuation element 500 or 120 may be actuated by actuating a corresponding drive member 400.

Components of the force transmission assembly 300 and other associated parts of the instrument 10 are described below in greater detail with reference to FIGS. 2-9. For organizational purposes and to assist in readability, the description includes subheadings for the various components that will be described. However, it should be understood that while in some embodiments, the various components are used together, other embodiments of force transmission assemblies may not necessarily include all the components discussed.

Force Transmission Assembly Housing

Figure 3:
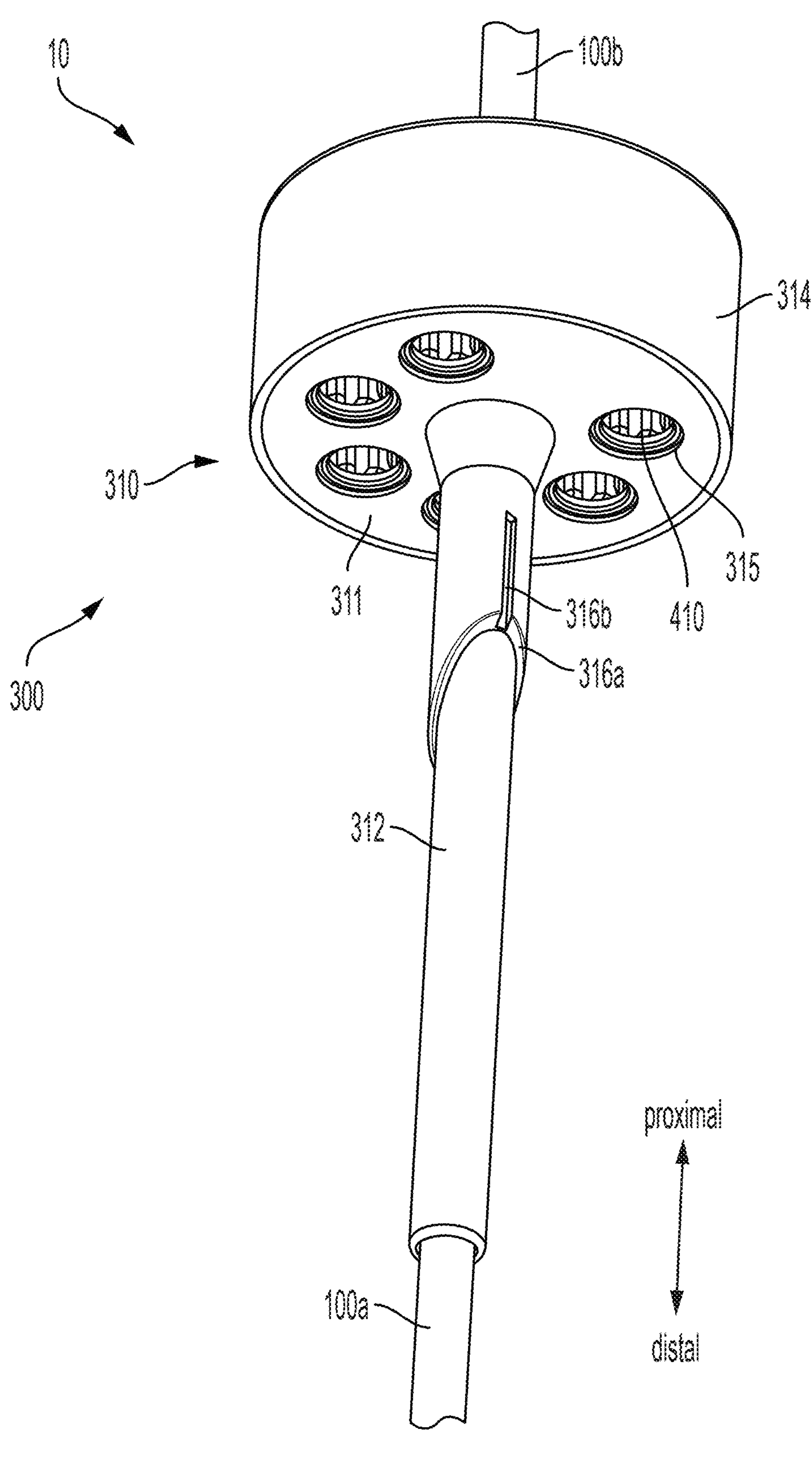
FIG. 3 is a perspective view of a transmission assembly housing and a portion of the shaft of the instrument of FIG. 2.

With reference to FIGS. 2-4, the force transmission assembly 300 comprises a housing 310. The housing 310 comprises a chassis 311, a sleeve 312 extending distally from the chassis 311, and a cover portion 314. The chassis 311 serves as a platform or a base that supports other components of the force transmission assembly 300, such as the drive members 400 described in further detail below. The chassis 311 and the cover portion 314 cooperate together to define a chamber in the housing 310 within which the drive members 400 and other components of the force transmission assembly 300 are housed.

In the embodiment of FIGS. 2-9, the chassis 311 also provides an interface for coupling the instrument 10 to a manipulator. Specifically, a distal face of the chassis 311, visible in FIG. 3, forms an interface for the instrument 10 that is mountable to a complementary interface of the manipulator (e.g., interface 73, described below with respect to FIG. 18). The chassis 311 may engage either directly with the manipulator, or the chassis 311 may engage indirectly with the manipulator via an intermediary device, such as a sterile adaptor that is interposed between the manipulator and the instrument 10 to provide a sterile barrier. As shown in FIG. 3, the distal face of the chassis 311 comprises openings 315 through which drive inputs 410 of the drive members 400 (visible in FIGS. 4 and 5) are accessible from an exterior of the chassis 311, for example from the distal side of the chassis 311 in the depicted embodiment. Corresponding drive outputs of the manipulator to which the instrument 10 is mounted (e.g., drive outputs 75, described below with respect to FIG. 18) may thus interact with the drive inputs 410 via the openings 315 to transfer driving forces to the drive inputs 410. The drive outputs of the manipulator may engage directly with the drive inputs 410, or they may be engaged indirectly via an intermediary, such as intermediate couplers of the sterile adaptor. The drive inputs 410 and the drive outputs (or intermediate couplers) may have complementary engaging surfaces, such as engaging surfaces with complementary groves and protrusions or other complementary anti-rotation features, such that when the drive inputs 410 are engaged with the drive outputs or intermediate couplers they are constrained to rotate together. In FIG. 3, the drive inputs 410 are shown as having receptacles into which complementary drive outputs or intermediate couplers are received, but in other embodiments, the drive inputs 410 may comprise protrusions configured to be received within complementary receptacles of the drive outputs or intermediate couplers, or any of a variety of other mating engagements to allow the drive inputs to engage with the corresponding drive outputs or intermediate couplers. In FIG. 3, the drive inputs 410 are shown as being wholly contained within the housing 310, but in other embodiments the drive inputs 410 may extend distally from the chassis 311 through the openings 315.

A sleeve 312 of the housing 310 surrounds the instrument shaft 100 and extends distally from the chassis 311. The sleeve 312 is configured to be insertable into a passage of a manipulator when the instrument 10 is mounted to the manipulator. The sleeve 312 facilities sealing of the workspace to prevent escape of pressurized fluid. The sleeve 312 may also comprise alignment features 316 to aid in alignment of the instrument 10 relative to the manipulator as the instrument 10 is mounted to the manipulator. For example, FIG. 3 illustrates two alignment features 316, namely first alignment feature 316*a* and second alignment feature 316*b*. The first alignment feature 316*a* comprises an angled surface portion forming a shoulder or series of shoulders extending circumferentially around the sleeve 312 and configured to engage with complementary surfaces of the manipulator as the sleeve 312 is inserted into the passage of the manipulator to provide progressively increasing alignment between the instrument 10 and the instrument holder the further the instrument 10 is inserted into the passage. The second alignment feature 316*b* may comprise one or more straight notches extending proximally from an apex of the first alignment feature 316*a* and generally parallel to a longitudinal axis of the instrument shaft 100. The second alignment feature 316*b* interacts with a complementary feature of the manipulator once the instrument 10 has been inserted sufficiently far into the passage. The first alignment feature 316*a* is configured such that they will bring the instrument 10 into an aligned orientation by the time the instrument 10 has advanced sufficiently into the passage for the second alignment features 316*b* to be engaged. The second alignment feature 316*b* then holds the instrument 10 in the aligned orientation as the instrument 10 continues to be advanced into the passage until a mounted position is reached. The initial alignment forced by the first alignment feature 316*a* may bring the drive inputs 410 into alignment with the corresponding drive outputs of the manipulator prior to coupling thereof, and then the continued advancement of the instrument thereafter while the second alignment feature 316*b* maintains the aligned orientation may enable the coupling between the drive inputs 410 and drive outputs to be completed.

In the illustrated embodiment, the sleeve 312 and the chassis 311 are integrally coupled together, or in other words they are both part of the same monolithic body. In other embodiments, the sleeve 312 and the chassis 311 are separately formed parts that are coupled together, for example, by mechanical fasteners, friction fitting, adhesive, welding, or other known joining techniques.

Drive Members—Overview

Turning now to FIGS. 4 and 5, embodiments of drive members 400 and other related components of the transmission assembly 300 will be described in greater detail. FIG. 4 comprises a perspective view of the transmission assembly 300 from a first side, with the cover portion 314 removed to show the drive members 400. The drive members 400 may be used as the drive members 24 described above. FIG. 5 comprises a perspective view of the transmission assembly 300 from a second side opposite the first side, with the cover portion 314 removed to show the drive members 400. The drive members 400 may be used as the drive members 24 described above.

As shown in FIGS. 4 and 5, the transmission assembly 300 comprises a plurality of drive members 400. The drive members 400 each actuate one or more actuation elements 500 or 120, which drives a corresponding degree of freedom of motion of the instrument 10. In particular, at least one drive member 400 drives an insertion degree of freedom of motion by actuating pullable actuation elements 500, and at least one other drive member 400 drives motion of a movable component 200 by driving rotation of a rotatory actuation element 120. In some embodiments, the transmission assembly 300 may also include one or more additional drive members 400 that drive additional degrees of freedom of motion, for example by driving pullable actuation elements 500. More specifically, in the embodiment illustrated in FIGS. 4-9, the transmission assembly 300 comprises six drive members 400, with a first drive member 400_1 being configured to drive an insertion degree of freedom of motion, a drive member 400_6 configured to drive the rotational actuation element 120, and drive members 400_2 to 400_5 to drive other degrees of freedom of motion of the instrument 10. The drive member 400_1 may also be referred to herein as an "insertion drive member," and the other drive members 400 may also be referred to as "non-insertion drive members." Although five non-insertion drive members 400_2 to 400_6 are illustrated, it should be understood that any number of non-insertion drive members equal to or greater than one may be included.

As noted above, each drive member 400 drives a corresponding degree of freedom of motion of the instrument 10 by actuating at least one corresponding actuation element 500 or 120. In particular, as shown in FIG. 4, each drive member 400 comprises a drive shaft 420 about which the drive member 400 is rotatable relative to the chassis 311, with rotation of the drive member 400 about its drive shaft 420 actuating the corresponding actuation element 500 or 120 (i.e., causing the corresponding actuation elements 500 to pay out or draw in, depending on the direction of rotation, or causing the actuation element 120 to rotate). The drive shaft 420' of the drive member 400_6 may extend outside of the transmission assembly 300, and thus may also be referred to herein as an extended drive shaft 420'.

As shown in FIGS. 3-5, each drive member 400 also comprises a drive input 410 coupled to the drive shaft 420 such that the drive shaft 420 is constrained to rotate with the drive input 410. As noted above, in a mounted state of the instrument 10 to a manipulator, the drive input 410 receives driving forces from a drive output of the manipulator, and these driving forces drive rotation of the drive shaft 420 coupled to the drive input 410. (The driving forces may also be referred to as torques, because they induce rotational motion; herein, references to "force" are not limited to forces urging linear motion, and can include torques that urge rotational motion.) As shown in FIG. 4, a distal end portion of each drive shaft 420 is coupled to a drive input 410, which is rotatably coupled to the chassis 311. In addition, a proximal end portion of the drive shafts 420 may be rotatably coupled to a proximal support (not illustrated). Thus, each drive shaft 420 has one rotational bearing at a proximal end portion thereof and another rotational bearing at the distal end portion thereof in the form of the chassis 311 (via the drive inputs 410).

In addition to the drive input 410 and the drive shaft 420, each of the drive members 400_1 to 400_5 also comprises one or more actuation element handling components that couple the drive member 400 to at least one corresponding actuation element 500. The actuation element handling components of each drive member 400_1 to 400_5 are coupled to the drive shaft 420 thereof such that rotation of the drive shaft 420 causes the actuation element component to actuate the corresponding actuation element(s) 500 coupled thereto. In the case of the insertion drive member 400_1, the actuation element handling component comprises a rotatable drum or capstan 415 (hereinafter drum 415). In the case of the non-insertion drive members 400_2 and 400_5, their respective actuation element handling components comprise actuation transfer mechanisms 430. The actuation transfer mechanisms 430 may be used as the actuation element handling device 27 described above. In the case of the drive member 400_6, the extended drive shaft 420' is coupled to the rotational actuation element 120 via a gear mechanism 428 that may be housed in the gear housing 501 at the distal end portion **100*b* of the instrument shaft 100. These actuation element handling components and their interactions with the actuation elements 500 and 120** are described in greater detail below.

Insertion Drive Member and Corresponding Actuation Elements

With reference to FIGS. 4-6, an embodiment of an insertion drive member 400_1 will be described in greater detail below. FIG. 6 is a schematic diagram showing how actuation elements 500 are routed and connected to other components of the instrument, such as the drive members 400 of the force transmission assembly 300. The diagram in FIG. 6 is not intended to show actual sizes, actual shapes, actual or relative physical locations of components, or the actual paths taken by actuation elements 500, but instead FIG. 6 shows the connections and routing schematically and in simplified form to aid understanding. It should be understood that additional handling components besides those illustrated, such as pulleys, could be interposed in the actuation element paths, and in actual implementations the actuation element paths may deviate from those shown. Moreover, in FIG. 6 the instrument shaft 100 is indicated schematically by dashed lines, and different portions of the shaft 100 are shown with different widths to facilitate illustration of the disposition of the actuation elements 500 relative to the shaft 100 in and along different portions thereof, but it should be understood that the illustrated dimensions of the shaft 100 are not meant to be accurate or to scale.

As noted above, the insertion drive member 400_1 comprises a rotatable drum 415 to actuate (i.e., draw in and pay out) the actuation elements 500 that are coupled to the drum 415. The term "drum" as used herein is intended to refer broadly to any component having a rotational axis and a bearing surface extending generally circumferentially (although not necessarily in a perfect circle) around the rotational axis around which flexible pullable actuation elements 500 (such as cables, wires, filaments, chains, straps, belts, ropes, etc.) can be wound by rotation of the drum 415. The drum 415 may be configured as any of a variety of rotational drive devices, such as, for example, a cylinder, a spool, a capstan, a windlass, a winch, or the like. The drum 415 may have guide elements, such as grooves and/or ridges, to guide actuation elements 500 as they wind around the drum 415, or the drum 415 may omit such guide elements and have a generally smooth surface.

Multiple pullable actuation elements 500 are coupled to and wound around drum 415 such that rotation of the drum 415 draws in or pays out the actuation elements 500, depending on direction of rotation. As shown in FIGS. 4-6, one or more of the actuation elements 500 that are coupled to the drum 415 are also coupled to and actuatable by a non-insertion drive member 400. But, as will be described in more detail below, these actuation elements 500 can move past or through the non-insertion drive members 400 to which they are coupled when the actuation elements 500 are actuated by the drum 415 (due to the actuation transfer mechanisms 430, described below); therefore, the non-insertion drive members 400 can be ignored when considering the operation of the insertion drive member 400_1.

At least one of the actuation elements 500 coupled to the drum 415 (e.g., actuation element 500_1) extends proximally from the transmission assembly 300 and is coupled (directly or indirectly) to a proximal portion **100*b* of the shaft 100 at a position proximal of the force transmission assembly 300, as shown schematically in FIG. 6. Thus, drawing in these one or more proximally coupled actuation element 500 causes the shaft 100 to translate distally relative to the transmission assembly 300. At least one other of the actuation elements 500 coupled to the drum 415 (e.g., actuation elements 500_2 to 500_5) extends distally from the force transmission assembly 300 and is coupled (directly or indirectly) to a distal portion 100***a* of the shaft 100 at a position distal of the force transmission assembly 300, as shown schematically in FIG. 6. Thus, drawing in these one or more distally coupled actuation element 500 causes the causes the shaft 100 to translate proximally relative to the transmission assembly 300.

As shown in FIGS. 4 and 6, each actuation element 500 that is coupled to the proximal portion 100*b* of the instrument shaft 100 (e.g., actuation element 500_1) is wound around the drum 415 in an opposite direction than the actuation elements 500 that are coupled to the distal portion 100*b* of the shaft 100 (e.g., actuation elements 500_2 to 500_5). Therefore, rotation of the drum 415 in one direction draws in the actuation element(s) 500 that are coupled to the proximal portion 100*b* (e.g., actuation element 500_1) while simultaneously paying out the actuation elements 500 coupled to the distal portion 100*a* (e.g., actuation elements 500_2 to 500_5), and rotation of the drum 415 in an opposite direction has the opposite effect. Thus, the insertion drive member 400_1 is actuatable to control the insertion degree of freedom of motion of the instrument 10, or in other words to drive relative motion of the shaft 100 and the force transmission assembly 300.

The coupling of actuation elements 500 to the drum 415 and the actuation thereof to control the insertion degree of freedom of motion is described in general terms above. A specific example embodiment of how the actuation elements 500 and drum 415 may be configured will now be described below with continued reference to FIGS. 4-6. In the embodiment illustrated in FIGS. 4-6 the one or more actuation elements 500 that are coupled to the proximal portion 100*b* of the shaft 100 comprise a single actuation element, namely the actuation element 500_1. In some embodiments, the actuation element 500_1 is not coupled to any of the non-insertion drive members 400. As shown in FIGS. 5 and 6, the actuation element 500_1 is routed from the drum 415 to a waterfall pulley 530 that has an axis of rotation perpendicular to the axis of rotation of the drum 415. The waterfall pulley 530 redirects the actuation element 500_1 to extend proximally along the shaft 100. The actuation element 500_1 extends along the shaft 100, for example via a groove 110 (see FIG. 5) in an outer surface of the shaft 100. As shown schematically in FIG. 6, the actuation element 500_1 extends proximally until it reaches a coupling location 565_1 at which the actuation element 500_1 is coupled either directly or indirectly to the shaft 100. The coupling location 565_1 may be part of the shaft 100 or part of some other component that is itself coupled (directly or indirectly) to the shaft 100, and may be located on an outside of the shaft 100 as shown in FIG. 6 or may be located inside of the shaft 100 in other embodiments. The coupling location 565_1 may be located somewhere along the proximal portion 100*b* of the shaft 100, for example at a position that remains proximal of the transmission assembly 300 throughout a range of motion of the shaft 100 and transmission assembly 300 relative to one another. Thus, when the distal insertion actuation element 500_1 is drawn in, it pulls on the shaft 100 and urges the shaft 100 to move in the distal direction.

In the embodiment illustrated in FIGS. 4-6, the one or more actuation elements 500 that are coupled to the distal portion 100*a* of the shaft 100 comprise multiple actuation elements, namely the actuation elements 500_2 to 500_5. In this embodiment, all of the actuation elements 500_2 to 500_5 that are coupled to the distal portion 100*a* of the shaft 100 are coupled not only to the drum 415 but also to a corresponding one of the non-insertion drive members 400_2 to 400_5. Specifically, as shown in FIGS. 4-6, the actuation elements 500_2 to 500_5 have respective proximal end portions coupled to the drum 415, extend from the drum 415 to couple with actuation transfer mechanisms 430 (described below) of the drive members 400_2 to 400_5, extend from the drive members 400_2 to 400_5 to corresponding waterfall pulleys 530, and then from the waterfall pulleys 530 extend distally along and through the shaft 100 to the distal portion 100*a* of the shaft 100 where respective distal end portions of the actuation elements 500_2 to 500_5 are coupled to coupling points 565_2 to 565_5, respectively, as shown in FIG. 6. The coupling points 565_2 to 565_5 may be coupled directly or indirectly with the distal portion 100*a* of the shaft 100. In the embodiment in FIGS. 2-9, the coupling points 565_2 to 565_5 are part of one or more articulable structures 230, which are coupled to the shaft 100. The coupling points 565_2 to 565_5 and how they may be used to drive articulation of the articulable structure 230 will be described in greater detail below, but in relation to the insertion degree of freedom of motion being presently described the relevant aspect of the coupling points 565_2 to 565_5 is that they are configured such that when all of the actuation elements 500_2 to 500_5 are simultaneously drawn in at the same rate, then the one or more articulable structures 230 are locked in whatever their current position is by equal and opposite tension applied thereto from opposing pairs of the actuation elements 500_2 to 500_5. Thus, when all of the actuation elements 500_2 to 500_5 are simultaneously drawn in, the one or more articulable structures 230 do not articulate and instead a net force in the proximal direction is applied to the articulable structures 230, and hence also to the shaft 100 to which they are coupled, resulting in proximal translation of the shaft 100. Because the actuation elements 500_2 to 500_5 are all wrapped around the drum 415 in a same direction, rotation of the drum 415 in one direction (e.g., clockwise in FIG. 4) draws in all of the actuation elements actuation elements 500_2 to 500_5 simultaneously, resulting in proximal translation the shaft 100 along the insertion axis relative to the transmission assembly 300.

Thus, the actuation element 500_1 drives the insertion degree of freedom of motion along one direction when the insertion actuation element 400_1 is rotated in a first direction to draw in the actuation element 500_1, and the actuation elements 500_2 to 500_5 collectively drive the insertion degree of freedom of motion along an opposite direction when the insertion drive member 400_1 is rotated in a second direction to draw in the actuation elements 500_2 to 500_5.

During actuation of the insertion degree of freedom of motion, the rotational actuation element 120 floats relative to the transmission assembly 300 and remains stationary relative to the instrument shaft 100. This is important to ensure that actuation of the insertion degree of freedom of motion does not inadvertently cause actuation of the movable component 200 that is driven by the actuation element 120, such as a component of the end effector 210. The actuation element 120 is held stationary relative to the shaft 100 while the shaft 100 is driven to move relative to the transmission assembly 300 by a gear mechanism 428 (described in greater detail below with reference to FIGS. 8A and 8B) coupled to the actuation element 120 and a proximal portion 100*b* of the shaft 100.

In some embodiments, the transmission assembly 300 may include another actuation element (not illustrated), which is dedicated for driving the proximal translation of the shaft 100 along the insertion axis and not for driving any other movable components 200. For example, such an actuation element may be coupled to the drum 415 and extend distally from the force transmission assembly 300 to couple directly to a distal portion 100*b* of the shaft 100, such that pulling in the actuation element 500 causes proximal translation of the shaft 100.

Non-Insertion Drive Members with Actuation Transfer Mechanisms

Figure 7B:
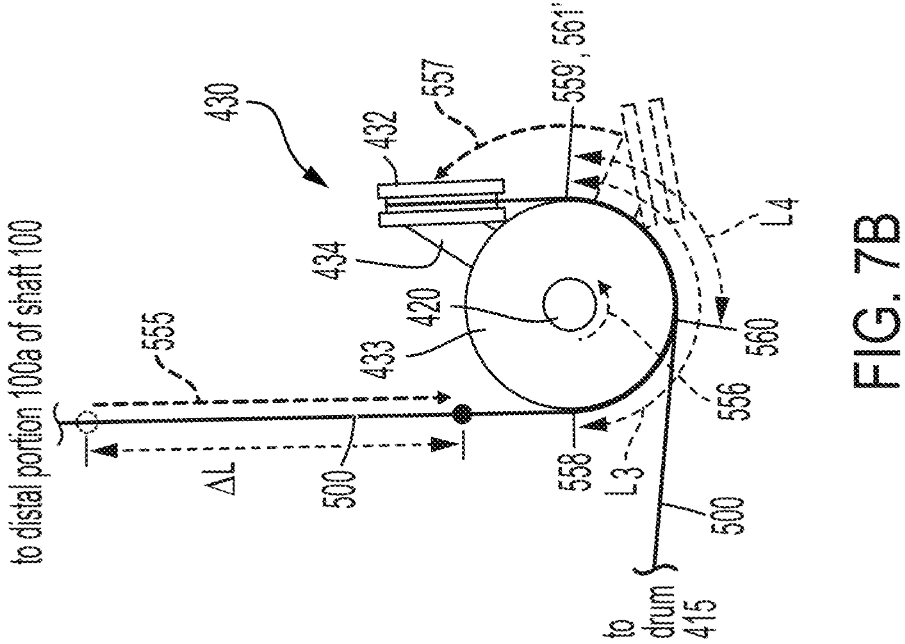
FIG. 7B is a plan view of the actuation transfer mechanism of FIG. 7A in a second state.
Figure 7A:
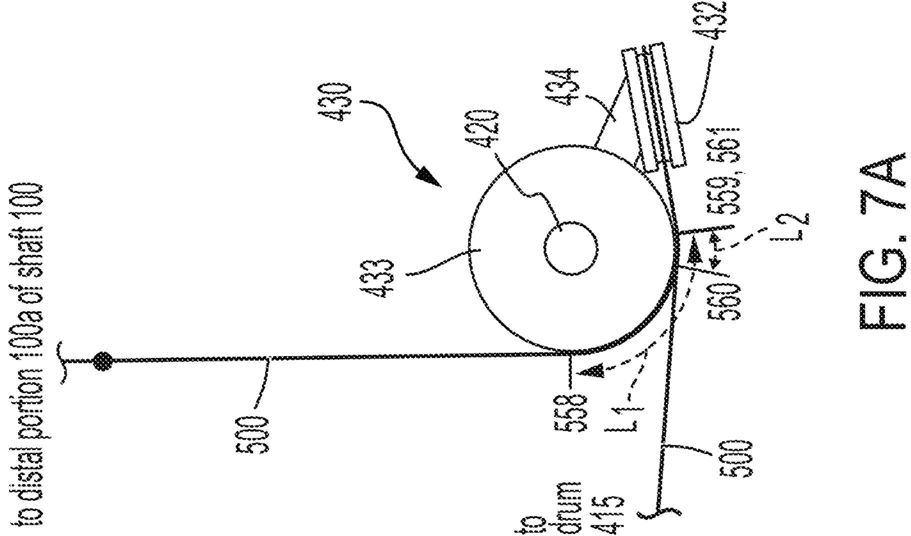
FIG. 7A is a plan view of an embodiment of an actuation transfer mechanism of the instrument of FIG. 2 in a first state.
Figure 7D:
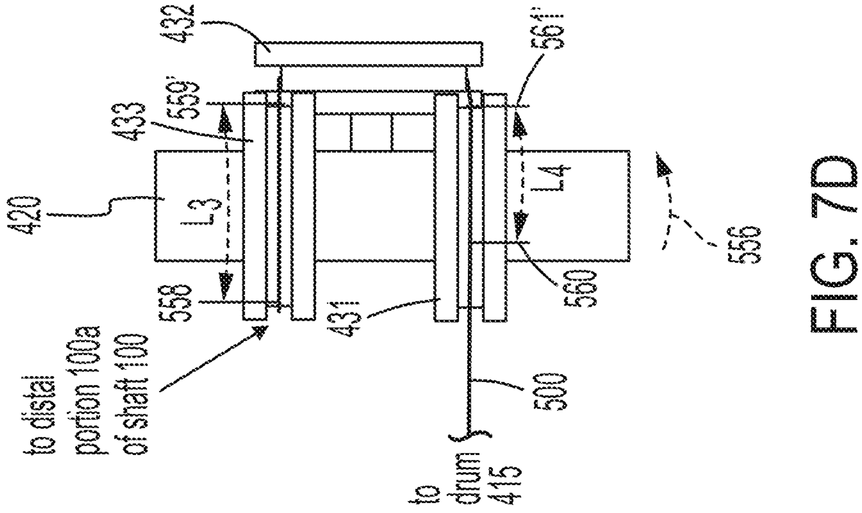
FIG. 7D is a side view of the actuation transfer mechanism of FIG. 7A in the second state.

With reference to FIGS. 4-7D, the non-insertion drive members 400 that have an actuation transfer mechanism 430 will be described in greater detail below. FIGS. 7A and 7B illustrate plan views of an actuation transfer mechanism 430 (described in greater detail below) in two states from a perspective above (i.e., proximal of) the actuation transfer mechanism 430. FIGS. 7C and 7D illustrate side views of the actuation transfer mechanism 430 in the states of FIGS. 7A and 7B, respectively.

As noted above, at least some of the non-insertion drive members 400 comprise one or more actuation transfer mechanisms 430 to couple with and actuate actuation elements 500, as shown in 4-7D. Specifically, in the embodiment of FIGS. 4-6, the non-insertion drive members 400_2 to 400_5 each comprise an actuation transfer mechanism 430.

An actuation transfer mechanism 430 of a given drive member 400 is configured to allow both the insertion drive member 400_1 and the given non-insertion drive member 400_2 to 400_5 to actuate the same actuation element 500 independently of one another. In other words, if the drum 415 is held stationary while a given drive member 400_2 to 400_5 is rotated, the actuation transfer mechanism 430 of the given drive member 400 actuates (pays out or draws in) the corresponding actuation element cable 500. Likewise, if the drum 415 is rotated while the given drive member 400_2 to 400_5 is held stationary, the actuation transfer mechanism 430 allows the drum 415 to actuate the actuation element 500. Thus, the actuation transfer mechanism 430 can allow a transfer of actuation of the same actuation element 500 between the drum 415 and the corresponding drive member 400_2 to 400_5 to which the actuation element 500 is coupled.

As shown in FIGS. 4 and 7A-7D, in some embodiments an actuation transfer mechanism 430 comprises a first pulley 431 rotatably coupled to and coaxial with the drive shaft 420, a second pulley 432 radially offset from the drive shaft 420 and having an axis of rotation oriented angled relative to (e.g., transverse to) an axis of rotation of the drive shaft 420, and a third pulley 433 rotatably coupled to and coaxial with the drive shaft 420. The second pulley 432 is attached to an arm member 434 coupled to and extending generally radially from the drive shaft 420 and constrained to rotate with the drive shaft 420.

The manner in which the actuation elements 500 couple with the actuation transfer mechanisms 430 is described below using the actuation transfer mechanism 430 of the drive member 400_3, as shown in FIGS. 4 and 5, as an example. The same principles apply to the other actuation transfer mechanisms 430 and their respectively corresponding actuation elements 500. As shown in FIGS. 4 and 5, the actuation element 500_3 is routed from the drum 415 to the first pulley 431 such that the actuation element 500_3 begins to wrap around the first pulley 431 and hence also the drive shaft 420 in a first direction, then the actuation element 500_3 is looped around the second pulley 432 and redirected back to the third pulley 433 to wrap around third pulley 433 and hence the drive shaft 420 again in a second direction opposite the first direction. From the third pulley 433, the actuation element 500_3 extends to a waterfall pulley 530, which redirects the actuation element 500_3 to extend along the shaft 100.

The actuation transfer mechanisms 430 as described above allow the actuation elements 500 coupled thereto to move past or through the non-insertion drive members 400 when actuated by the insertion drive member 400_1. For example, if the actuation element 500_3 is actuated by the insertion drive member 400_1, the pulleys 431, 432, and 433 of the actuation transfer mechanism 430 of the drive member 400_3 rotate around their respective axes in response to actuation of the actuation element 500_3, thereby allowing the actuation element 500_3 to be paid out or drawn in through the actuation transfer mechanism 430 without actuation (rotation) of the drive member 400_3. Thus, though the drive member 400_3 is held stationary, the actuation element 500_3 can nevertheless be actuated, for example by the insertion drive member 400_1. In other words, the actuation transfer mechanism 430 allows the insertion drive member 400_1 to actuate the actuation element 500_3 independently of actuation of the drive member 400_3. The same is true of the other actuation transfer mechanisms 430 and their respectively corresponding actuation elements 500. Thus, the actuation transfer mechanisms 430 allow the insertion drive member 400_1 to actuate all of the actuation elements 500 coupled thereto simultaneously to drive the insertion degree of freedom of motion independently of actuation of any of the drive members 400_2 to 400_5.

On the other hand, the actuation transfer mechanism 430 as described above also allows the drive members 400 to actuate their respectively corresponding actuation elements 500, notwithstanding the fact that the actuation elements 500 are free to move through the actuation transfer mechanisms 430. Returning to the actuation transfer mechanism 430 of the drive member 400_3 as an example, when the drive shaft 420 of the drive member 400_3 is rotated, this causes the arm 434 of the actuation transfer mechanism 430 to also rotate with the shaft 420, and this causes the second pulley 432 coupled to the arm 434 to revolve around the drive shaft 420. Because the actuation element 500_3 is looped around the second pulley 432, the revolution of the second pulley 432 around the drive shaft 420 pays out or draws in the actuation element 500_3, depending on the direction of motion. Specifically, revolution of the second pulley 432 around the drive shaft 420 in a one direction, increases the amount of the actuation element 500_3 that is wound around the first and third pulleys 431 and 433, thus drawing in the actuation element 500_3. Conversely, revolution of the second pulley 432 around the drive shaft 420 in an opposite direction decreases the amount of the actuation element 500_3 that is wound around the first and third pulleys 431 and 433, thus drawing in the actuation element 500_3. Thus, the drive member 400_3 can actuate the actuation element 500_3 even if the insertion drive member 400_1 is held stationary. The same is true of the other actuation transfer mechanisms 430 and their respectively corresponding actuation elements 500. Thus, the actuation transfer mechanisms 430 allow the non-insertion drive members 400_2 to 400_5 to independently actuate their corresponding actuation elements 500, independently of the insertion drive member 400_1.

Figure 7C:
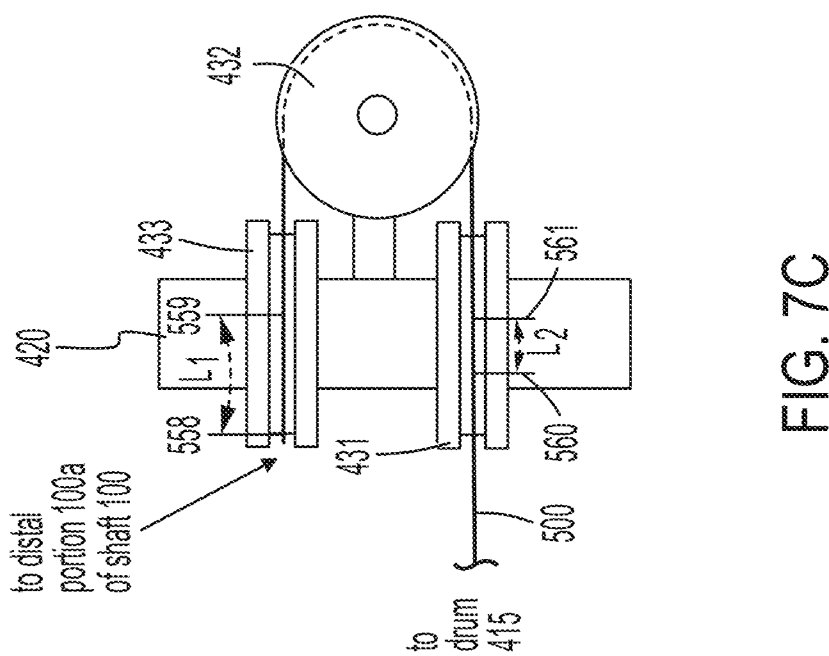
FIG. 7C is a side view of the actuation transfer mechanism of FIG. 7A in the first state.

The manner in which a non-insertion drive member 400 actuates an actuation element 500 via the actuation transfer mechanism 430 can be better understood by considering FIGS. 7A-7D, which illustrate schematically and in greater detail an actuation transfer mechanism 430. FIGS. 7A and 7B illustrate the actuation transfer mechanism 430 in a plan view from a perspective proximal of the actuation transfer mechanism 430, while FIGS. 7C and 7D illustrate a side view of the actuation element 430. In FIGS. 7A and 7C, the actuation transfer mechanism 430 is in a first state, and in FIGS. 7B and 7D the actuation transfer mechanism 430 is in a second state, in which the drive shaft 420 has been rotated counterclockwise (in the view of the figure) relative to the first state, as indicated by the arrow 556. The rotation of the drive shaft 420 causes the second pulley 432 to revolve counterclockwise around the drive shaft 420, as indicated by the arrow 557 in FIGS. 7B and 7D. In the first state shown in FIGS. 7A and 7C, the portion of the actuation element 500 that is wound around the third pulley 433 has a length $L_1$ measured from the location where the actuation element 500 initially contacts the third pulley 433 (location 558) to where it leaves the third pulley 433 (location 559) to extend to the second pulley 432. In addition, the portion of the actuation element 500 that is wound around the first pulley 431 has a length $L_2$ measured from where the actuation element 500 initially contacts the first pulley 431 (location 560) to where the actuation element 500 terminates contact with the first pulley 431 to extend to the second pulley 432 (location 561). In the second state shown in FIGS. 7B and 7D (after rotation of the drive shaft 420), the portion of the actuation element 500 that is wound around the third pulley 433 has a length $L_3$ measured from where the actuation element 500 initially contacts the third pulley 433 (location 558) to where the actuation element 500 terminates contact with the third pulley 433 to extend to the second pulley 432 (location 559'). In addition, the portion of the actuation element 500 that is wound around the first pulley 431 has a length $L_4$ measured from where the actuation element 500 initially contacts the first pulley 431 (location 560) to where the actuation element 500 terminates contact with the first pulley 431 to extend to the second pulley 432 (location 561'). As can be seen by comparing the lengths $L_1$ and $L_2$ illustrated in FIG. 7A with the lengths $L_3$ and $L_4$ illustrated in FIG. 7B, the rotation of the drive member 400 about the drive shaft 420 increases the total length of the actuation element 500 that is wound around the first and third pulleys 431 and 433. Specifically, the total length of the actuation element 500 that is wound around the first and third pulleys 431 and 433 in the first state is $L_1+L_2$, while in the second state it is $L_3+L_4$, where $L_4>L_2$ and $L_3>L_1$. Thus, the total length of the actuation element 500 that is wound around the first and third pulleys 431 and 433 has increased by an amount $\Delta L=L_3+L_4-(L_1+L_2)$ between the first and second states. Because one end portion of the actuation element 500 is attached to the drum 415 and thus held stationary, the other end portion of the actuation element 500, which is attached to a distal portion 100*a* of the shaft 100 (e.g., via a movable component 200), will be drawn in by the distance $\Delta L$ to provide for the increased length of the actuation element 500 wrapped round the first and third pulleys 431 and 433. The opposite would occur if the drive shaft 420 were rotated in the opposite direction (clockwise in the view of FIGS. 7A-7B), i.e., the length of the cable 500 wound around the pulleys 431 and 433 would shorten, resulting in the actuation element 500 paying out.

The pulleys 431, 432, and 433 are rotatable around their axes of rotation, which may reduce friction and makes actuation of the actuation elements 500 easier. However, in some embodiments, one, some, or all of the pulleys 431, 432, and 433 could be replaced with non-rotating bearings. Operation of the actuation transfer mechanism 430 would be the same in such an embodiment, except that the actuation element 500 would slide relative to the bearings rather than the pulleys 431, 432, and 433 rotating. This may result in increased friction, but in some circumstances this may be acceptable.

The actuation transfer mechanism 430 of one drive member 400 may have a reversed configuration relative to the actuation transfer mechanism 430 of another drive member 400, meaning that the two actuation transfer mechanisms 430 are coupled to the drive shafts 420 of their respective drive members 400 such that rotation of the drive shafts 420 in the same direction causes the actuation transfer mechanisms 430 to actuate their corresponding actuation elements 500 and 500 in opposite directions, i.e., paying out one while drawing in the other, and vice versa. For example, with reference to FIG. 4, the actuation transfer mechanism 430 of the drive members 400_2 and 400_3 have reversed configurations relative to one another. The reversed configuration may be achieved, for example, by positioning the respective second pulleys 432 of the two actuation transfer mechanisms 430 to face in the same direction as one another when their respective arms 434 extend in opposite directions from one another, as shown in FIG. 4, or in other words, by positioning the respective second pulleys 432 on opposite sides of their respective arms 434 so as to face in opposite directions as one another when their respective arms 434 are aligned in the same direction.

As already noted above, in some embodiments, the actuation elements 500_2 to 500_5 are coupled to one or more articulable structures 230, and when all drawn in simultaneously, these actuation elements 500_2 to 500_5 lock articulation of the articulable structures 230 and drive translation of the shaft 100. However, when some of these actuation elements 500_2 to 500_5 are drawn in while others are simultaneously paid out, then the articulable structures 230 are driven to articulate along one or more degrees of freedom of motion, while the shaft 100 is held stationary.

Specifically, in the embodiment illustrated in FIG. 6, the articulable structure 230 comprises a wrist mechanism comprising two joints comprising a first link 231*a* pivotably coupled to shaft 100 to pivot along a first degree of freedom of motion (e.g., yaw) and a second link pivotably coupled to the first link 231*a* to pivot along a second degree of freedom of motion (e.g., pitch) substantially orthogonal to the first degree of freedom. (In FIG. 6, the links 231*a* and 231*b* appear to pivot in the same plane due to the simplified schematic nature of the drawing, but in practice they may pivot along different directions, for example similar to the articulable structure 1230 shown in FIG. 11). In this embodiment, a first pair of actuation elements 500_3 and 500_4 are coupled to coupling points 565_3 and 565_4 that are part of the first link 231*a* and a second pair of actuation elements 500_2 and 500_5 are coupled to coupling points 565_2 and 565_5 that are part of the second link 231*b*. Thus, simultaneous actuation of the actuation elements 500_3 and 500_4 in opposite directions by the drive members 400_3 and 400_4 causes first link 231*a* to pivot relative to the shaft 100 along the first degree of freedom, and simultaneously actuation of actuation elements 500_2 and 500_5 in opposite directions by the drive members 400_2 and 400_5 causes second link 231*b* to pivot relative to the first link 231*a* along the second degree of freedom.

In other embodiments, the articulable structure 230 comprises a wrist mechanism similar to that described above, but instead of pairs of the actuation elements 500 being coupled respectively to each link 231*a* and 231*b*, in these embodiments all four actuation elements 500_2 to 500_5 are coupled to the second link 231*b*, with the coupling points 565_2 to 565_5 being different points on the second link 231*b*. In such embodiments, the links 231*a* and 231*b* may be caused to pivot relative to the shaft 100 and one another by simultaneously actuating two or more of the actuation elements 500_2 to 500_5 in various combinations (the combinations depending on the desired articulation of the wrist and on how coupling points 565_2 to 565_5 are arranged).

In other embodiments, some or all of the coupling points 565_2 to 565_5 may be parts of other movable component 200 other than an articulable structure 230, parts of the shaft 100, or parts of some other component of the instrument 10 which is coupled to the shaft 100, such as any moveable components that may utilize a coordinated pair of pullable actuation elements to move the moveable component.

Non-Insertion Drive Member with Extended Drive Shaft

Figures 8A, 8B:
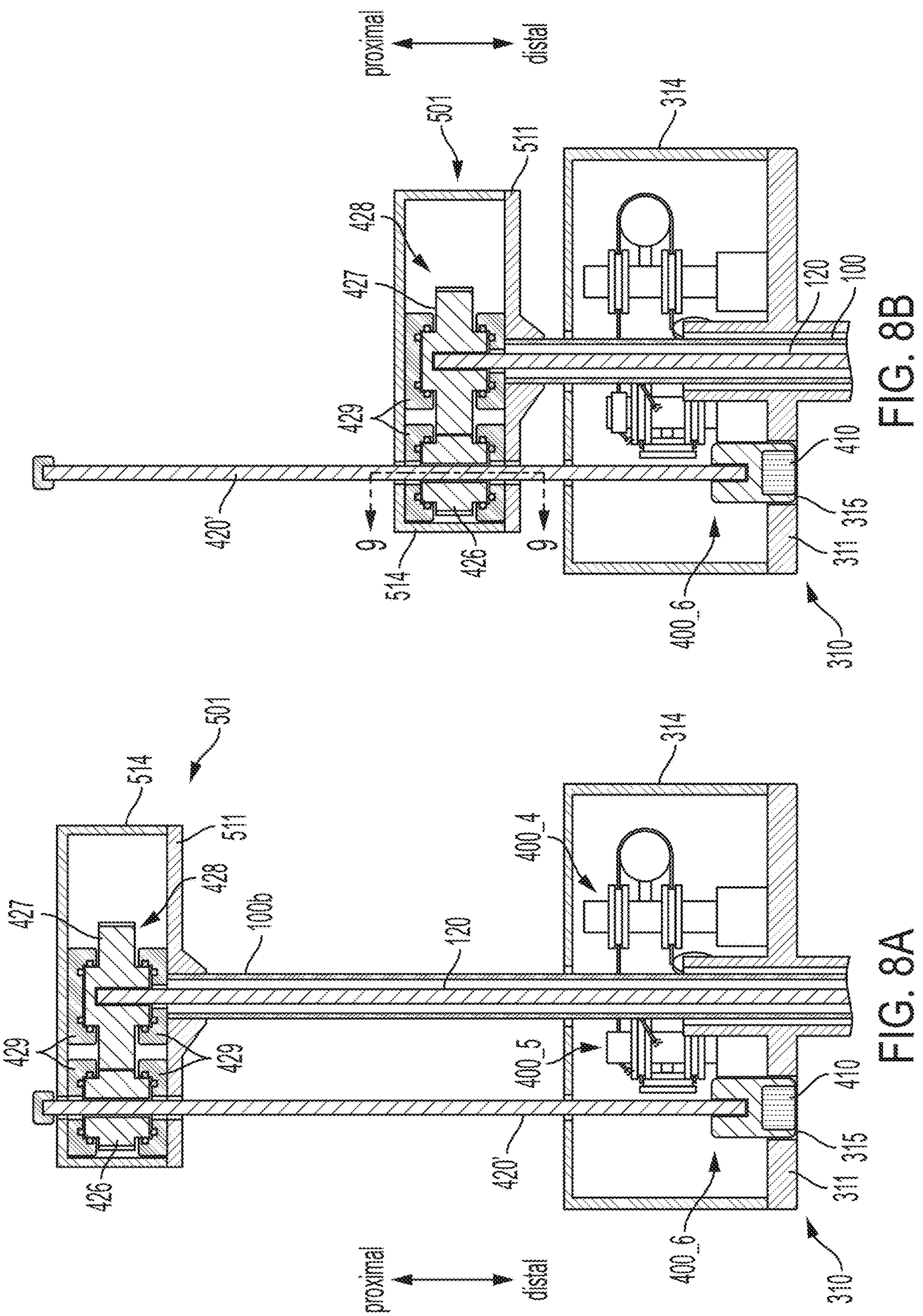
FIG. 8A is a sectional of the transmission assembly in a first state, with the section taken along the line 8-8 in FIG. 5.
FIG. 8B is a sectional view of the transmission assembly in a second state, with the section taken along the line 8-8 in FIG. 5.

As shown in FIGS. 2, 4, 8A, 8B, 9 and 10, the drive member 400_6 comprises an extended drive shaft 420' coupled to a drive input 410. The drive member 400_6 may be used as the drive member 24_3 described above. The extended drive shaft 420' of the drive member 400_6 may differ from the other drive shafts 420 of the other drive members 400 in that the extended drive shaft 420' extends distally outside of the transmission assembly 300 to couple with a gear assembly 428 in a gear housing 501 that is coupled to a proximal end portion 100*b* of the instrument shaft 100, as shown in FIGS. 8A and 8B.

The gear housing 501 may comprise a chassis 511 and cover 514 that enclose and support the gear assembly 428. The proximal portion 100*b* of the instrument shaft 100 is fixedly coupled to the chassis 511, and therefore the gear housing 501 is constrained to translate along with the instrument shaft 100. The gear assembly 428 comprises a first gear 426 and a second gear 427, which are engaged so as to rotate together. The first gear 426 is coupled to the extended drive shaft 420', while the second gear 427 is coupled to the rotational actuation element 120, as shown in FIGS. 8A and 8B. The gear housing 501 and gear assembly 428 may be used as the gear housing 35 and gear assembly 36 described above.

The extended drive shaft 420' is coupled to the first gear 426 in a manner that allows the first gear 426 to translate relative to and along the drive shaft 420' while also constraining the first gear 426 to rotate with the drive shaft 420'. For example, the extended drive shaft 420' may comprise one or more anti-rotation features, such as splines (grooves or protrusions extending along longitudinal dimension of the drive shaft 420'), that engage (directly or via an intermediary such as a ball bearing) with anti-rotation features on the first gear 426 to constrain the first gear 426 to rotate with the drive shaft 420' while allowing axial (longitudinal) translation of the first gear 426 relative to the drive shaft 420'. Specifically, the gear 426 comprises a central bore 465, with the anti-rotation features of the first gear 426 being provided on a surface of the gear 426 within the central bore 465 facing the drive shaft 420', and the anti-rotation feature of the extended drive shaft 420' being provided on an exterior surface of the drive shaft 420' facing the gear 426.

Figure 9:
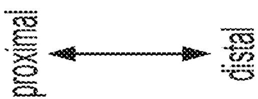
FIG. 9 is a sectional view of a portion of the transmission assembly, with the section taken along the line 9-9 in FIG. 8B.
Figure 9:
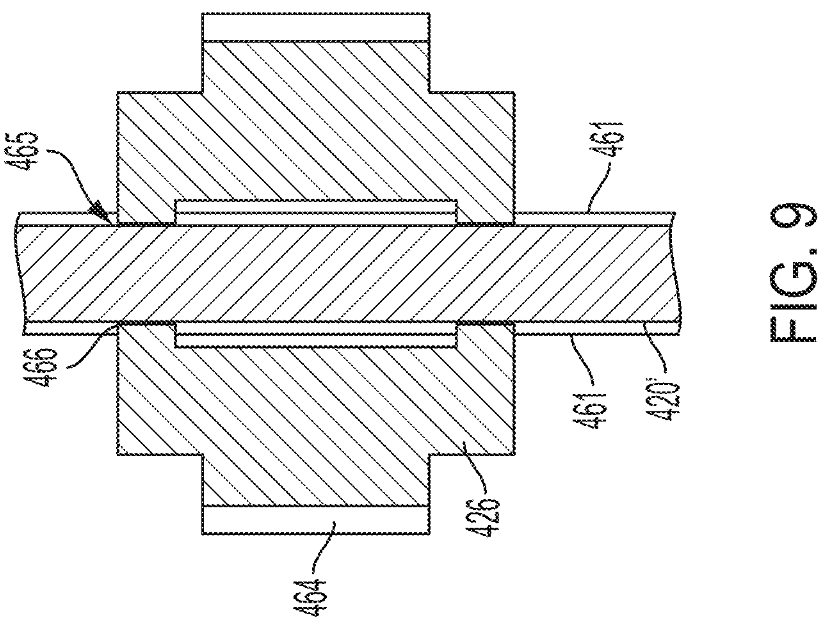
Figure 11:
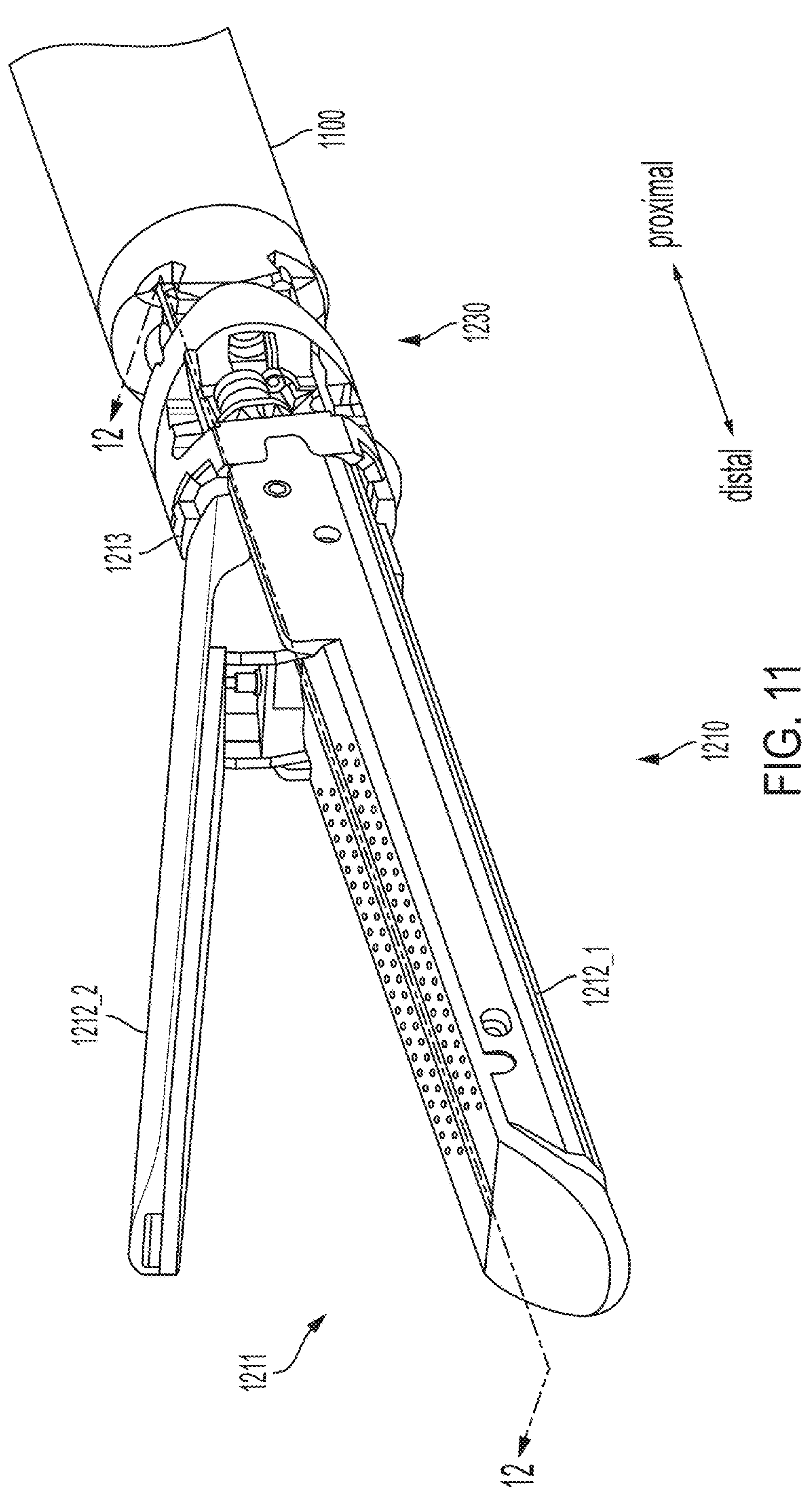
FIG. 11 is a perspective view of an embodiment of a distal portion of an instrument including the end effector.

In some embodiments the anti-rotation features of the gear 426 and drive shaft are coupled directly to one another without an intermediary bearing device. For example, as shown in FIG. 9, in some embodiments the anti-rotation feature of the extended drive shaft 420' comprise one or more grooves 461 in its outer surface that extend along the axial direction, and the anti-rotation feature of the first gear 426 comprise one or more complementary protrusions 466 that engage the grooves 461. The protrusions 466 are able to slide along the axial direction within the grooves 461, but the protrusions 466 and grooves 461 prevent relative rotation between the gear 426 and the extended drive shaft 420'. In some embodiments in which no intermediate bearing is provided between the gear 426 and the extended drive shaft 420', lubricants may be provided at the bearing surface to reduce friction. The materials of the gear 426 and drive shaft 420' may also be chosen so as to reduce sliding friction therebetween. Although the gear 426 is shown as having protrusions 466 while the drive shaft 420' is shown as having grooves, it should be understood that the reversed configuration could be used instead. Moreover, although two grooves 461 and four protrusions 466 are illustrated, this is a non-limiting example and any number of grooves and protrusions could be used as long as there is at least one of each.

Figure 10:
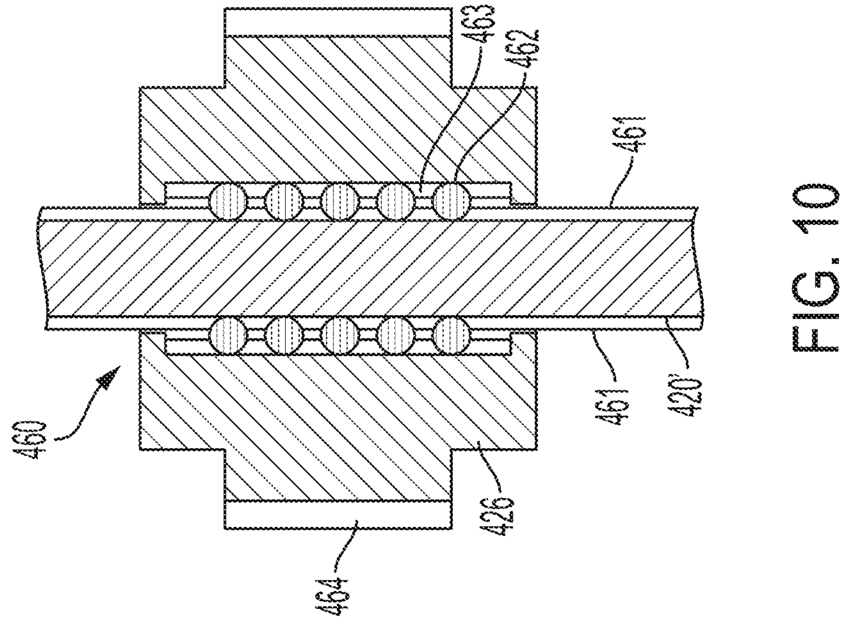
FIG. 10 is a cross section of another embodiment of the portion of the transmission assembly illustrated in FIG. 9, with the section taken along the line 9-9 in FIG. 8B.

In other embodiments, a spline mechanism, such as a ball spline mechanism or recirculating ball spline mechanism, may be used to couple the first gear 426 to the extended drive shaft 420'. For example, as shown in FIG. 10, a ball spline mechanism 460 may comprise a collection of ball bearings 462 captured between the first gear 426 and the extended drive shaft 420' such that one side of the ball bearing 462 is engaged with a groove 461 of the drive shaft 420' and the other side is engaged with a groove 463 of the first gear 426. Thus, the ball bearings 462 can roll in the axial direction along the grooves 461 and 463, allowing the gear 33 to translate relative to the extended drive shaft 31 with relatively low friction. However, the grooves 416 and 463 constrain the ball bearings 462 to prevent them from moving in circumferential directions around the extended drive shaft 420', and thus preventing relative rotation between the gear 426 and the extended drive shaft 320'. In a recirculating ball spline, the ball bearings may also be recirculated along a looped path (not shown), thus extending a range of translational motion of the ball spline mechanism.

As noted above, the second gear 427 is coupled with the proximal end portion of the rotational actuation element 120. More specifically, rotational actuation element 120 is fixedly coupled to the second gear 427 such that the rotational actuation element 120 is constrained to both rotate and translate along with the second gear 427. The first and second gears 426 and 427 may both be coupled to the gear housing 501 such that the first and second gears 426 and 427 are constrained to translate along with the gear housing 501, and hence with the instrument shaft 100 to which the gear housing 501 is coupled. For example, in some embodiments bearings 429 may be used to couple the gears 426 and 427 to the gear housing 501. The bearings 429 may comprise ball bearings, in some embodiments, to reduce friction. In other embodiments, the bearings 429 may be plain bearings. In still other embodiments, the bearings 429 may be omitted and the gears 429 may make contact directly with the chassis 511 and/or cover 514.

Thus, when the extended drive shaft 420' is rotated by the drive member 400_6, this causes the gears 426 to rotate, which causes the gear 427 to rotate, which causes the rotational actuation element 120 to rotate. Thus, the drive member 400_6 can actuate (i.e., rotate) the rotational actuation element 120 via the drive shaft 420' and the gear assembly 428.

Furthermore, when the insertion degree of freedom of motion is actuated by the drive member 400_1 such that the instrument shaft 100 translates relative to the transmission assembly 300, the gear housing 501 (including the gear assembly 428 housed therein) translates along with the shaft 100 because the gear housing 501 is fixedly coupled to the shaft 100. Because the rotational actuation element 120 is fixedly coupled to the second gear 427, when the gear assembly 428 translates along with the shaft 100, this causes the rotational actuation element 120 to also translate along with the instrument shaft 100. In other words, the rotational actuation element 120 is held translationally stationary relative the instrument shaft 100 by virtue of being fixedly coupled to the second gear 427, which is coupled to the gear housing 501, which in turn is coupled to the instrument shaft 100.

On the other hand, when the instrument shaft 100 is driven to translate relative to the transmission assembly 300, the extended drive shaft 420' does not translate along with the instrument shaft 100. Instead, the extended drive shaft 420' is translationally fixed relative to the transmission assembly 300. Thus, when the instrument shaft 100 is driven to translate relative to the transmission assembly 300, this causes the first gear 426 to translate relative to and along the extended drive shaft 420'. For example, FIG. 8A illustrates the instrument 10 in a first state in which the gear housing 501 and the transmission assembly 300 are spaced a distance apart, and FIG. 8B illustrates the instrument 10 in a second state in which the gear housing 501 has been moved closer to the transmission assembly 300 by way of the drive shaft 100 being driven to translate distally relative to the transmission assembly 300.

Thus, the drive shaft 420' and the gear assembly 428 allow for a driving connection to be maintained between the drive member 400_6 and the rotational actuation element 120 despite relative translation between the rotary actuation element 120 and the drive member 400_6 resulting from actuation of the insertion degree of freedom of motion.

End Effector and Rotational Actuation Element

Turning now to FIGS. 11-16B, various embodiments of end effectors and rotational actuation elements, which may be used as the end effector 210 and the rotational actuation element 120, will be described.

FIGS. 11-13B illustrate an end effector 1210. FIGS. 12A and 12B comprise cross sections taken along the line 12-12 in FIG. 11. FIGS. 12A and 12B comprise schematic cross sections taken along the line 13-13 in FIG. 11. FIG. 14 comprises an enlargement of the portion 14 in FIG. 11. The end effector 1210 is configured as a stapler and comprises a jaw mechanism 1211 comprising two jaws members 1212_1 and 1212_2 and a staple firing shuttle 1214 (also referred to as "shuttle 1214" and shown in FIGS. 12A and 12B). The jaw mechanism 1211 is coupled to a clevis 1213 such that one or both of the jaw members 1212 can pivot relative to the other jaw member 1212 and relative to the clevis 1213. With reference to FIGS. 12A-12B, the jaw member 1212_2 pivots while the other jaw member 1212_1 remains stationary. As shown in FIGS. 12A and 12B, the jaw member 1212_2 comprises a track 1215, which is engaged by a portion 217 of the shuttle 1214. The track 1215 comprises a garage portion 1218 and a sloped cam portion 216. As shown in FIG. 12A, when the shuttle 1214 is in a most proximal position, the portion 1217 is located in the garage portion 1218 of the track 1215, which causes the jaw member 1212_2 to be in an open position. In some embodiments, the portion 1217 may push against the jaw member 1212_2 when in the garage portion 1218, thus forcing the jaw member 1212_2 into the open position, while in other embodiments a spring or other biasing mechanism (not shown) may bias the jaw member 1212_2 toward the open position and the portion 1217 may allow the jaw member 1212_2 to be moved by the biasing mechanism into the open position when the portion 1217 is in the garage portion 218. If the shuttle 1214 is translated distally from the most proximal position, the portion 217 of the shuttle 1214 engages the cam portion 216, which causes the jaw member 1212_2 to pivot into a closed position, as shown in FIG. 12B, thus causing the jaw mechanism 1211 to grasp a material (if any) positioned between the jaw members 1212. As the shuttle 1214 continues to translate distally, the portion 217 travels along the track 215 and holds the jaw member 1212_2 in the closed state. Moreover, as the shuttle 1214 translate distally along the track 1215, a bottom portion 1219 of the shuttle 1214 engages with staples (not illustrated) contained within the bottom jaw member 1212_1 and fires the staples upward through openings in the jaw member 1212_1 into material grasped between the jaw members 1212_1 and 1212_2. In some embodiments, the staple firing shuttle 1214 may also comprise a blade 1220, which cuts material grasped by the jaw mechanism 211 as the staple firing shuttle 1214 is translated distally. After a staple firing procedure is completed, the shuttle 1214 may be translated proximally until it reaches the most proximal position, whereupon the portion 1217 of the shuttle 1214 enters the garage portion 1218 of the track and causes the jaw member 1212_2 to open.

Figures 12A, 12B:
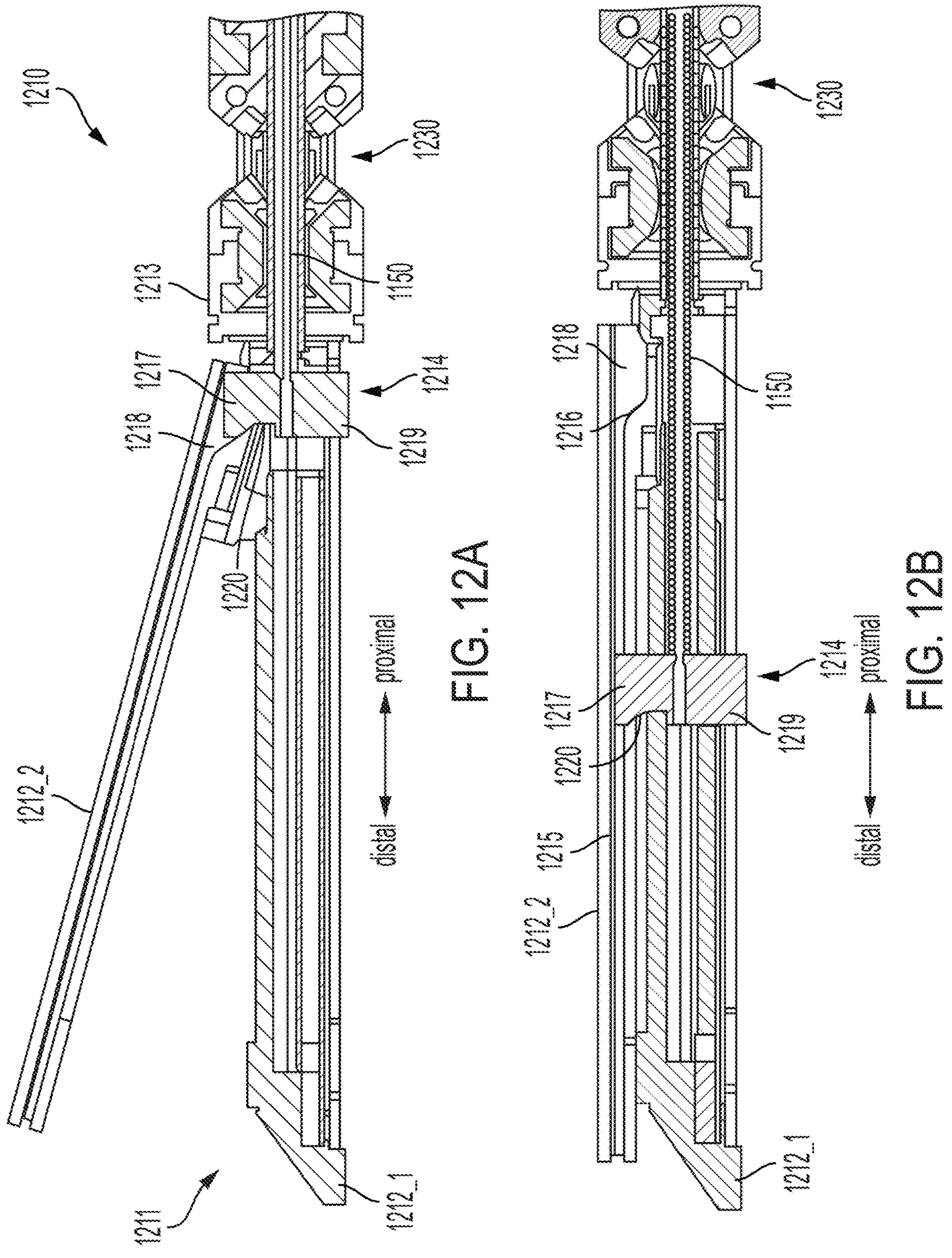
FIG. 12A is a cross section of FIG. 11 in a first state, with the section taken along the line 12-12.
FIG. 12B shows the distal portion of the instrument of FIG. 12A with the end effector in a second state.

As shown in FIGS. 12A and 12B, the translation of the shuttle 1214 is driven by a pushable actuation element 1150, which is coupled with the shuttle 1214. As shown schematically in FIGS. 13A and 13B, the pushable actuation element 1150 extends through an articulable structure 1230, which couples the end effector 1210 to an instrument shaft 1100. In some embodiments, the portion of the pushable actuation element 1150 that extends through the articulable structure 1230 is flexible in lateral directions (about its longitudinal axis), allowing it to bend with the articulable structure 1230. For example, in the embodiment illustrated in FIGS. 12A-14, the pushable actuation element 1150 comprises a push-coil 1151 with a cable 1152 running through a central channel of the push coil 1151, as shown in FIG. 14. This structure allows for the pushable actuation element 1150 to be flexible in all lateral directions while still being able to deliver relative strong pushing and pulling forces (even while bent). In other embodiments, other types of pushable actuation elements are used.

Figures 13A, 13B:
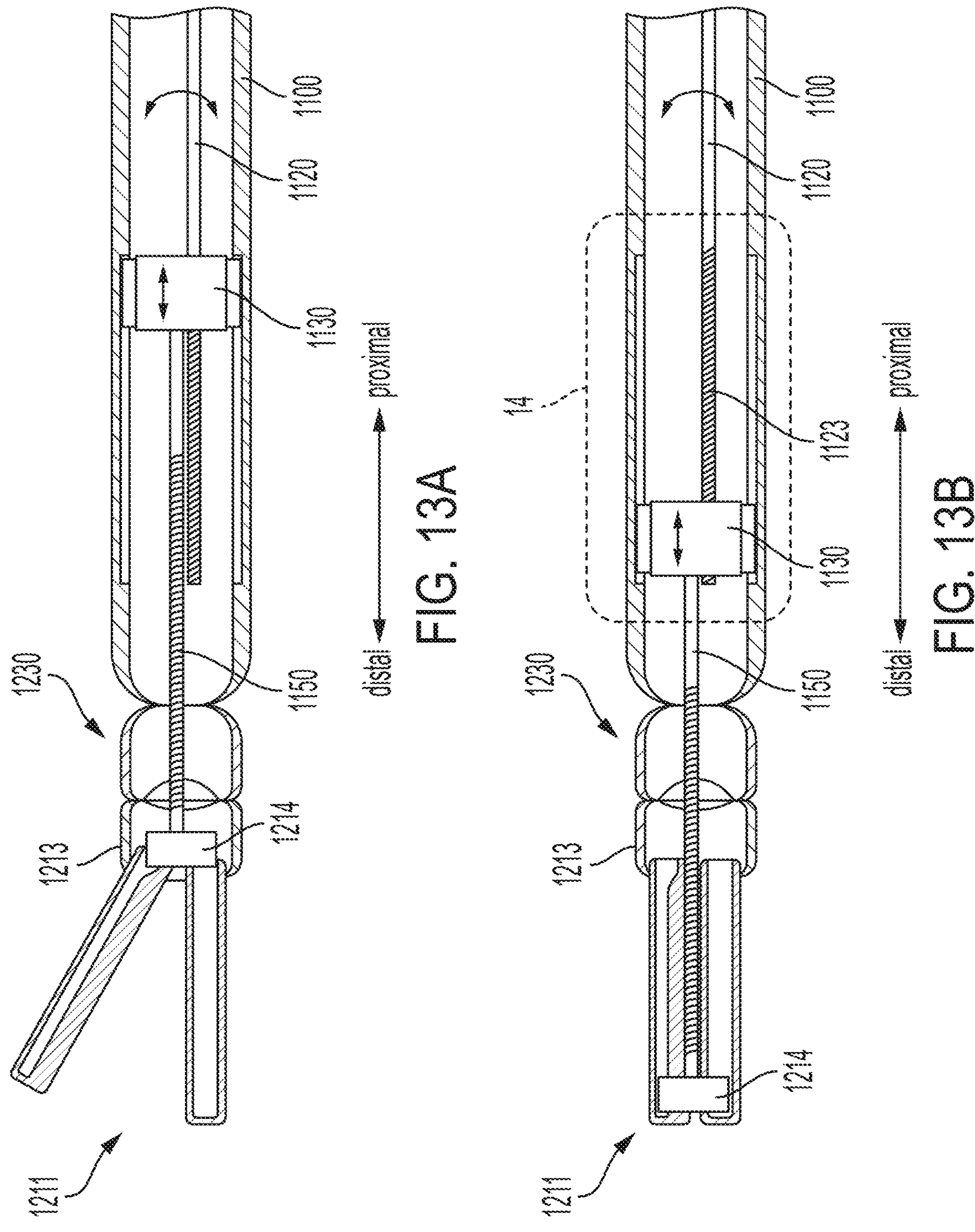
FIG. 13A is a schematic cross section of an embodiment of a distal portion of an instrument including an end effector in the first state, with the section taken along a longitudinal centerline.
FIG. 13B is a schematic cross section of the distal portion of the instrument of FIG. 13A in a second state, with the section taken along the line 13-13.
Figure 14:
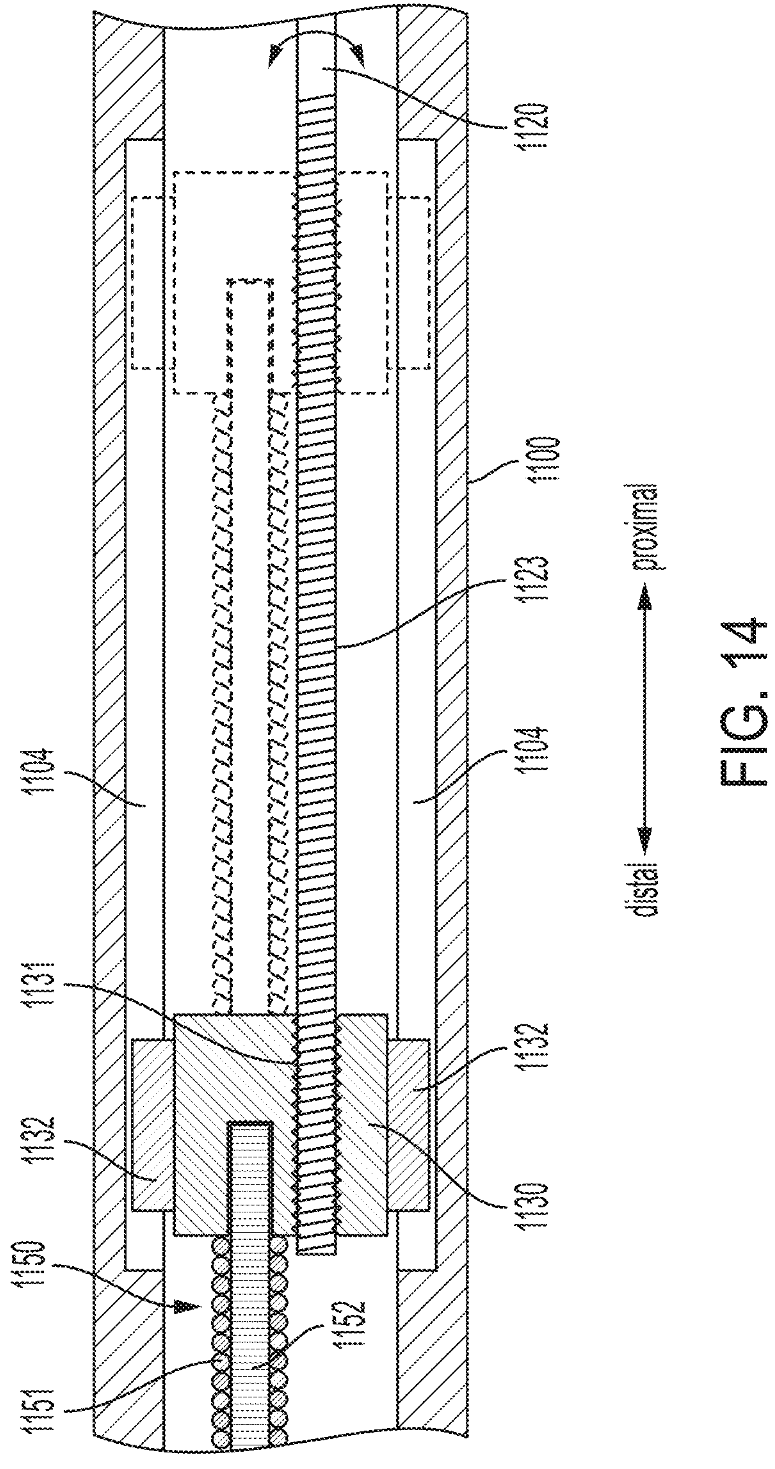
FIG. 14 is an enlarged view of the portion 14 of FIG. 13B.

As shown in FIGS. 13A-14, the pushable actuation element 1150 is coupled to the rotational actuation element 1220 via a follower nut 1130, which has internal threads 1131 that engage external threads 1123 of the rotational actuation element 1220 such that rotation of the rotational actuation element 1220 drives translation of the follower nut 1130 along the instrument shaft 1100. For example, FIG. 13A illustrate the follower nut 1130 in a most proximal position, while FIG. 13B illustrates the follower nut 1130 in a most distal position. The most proximal and distal positions of the follower nut 1130 are also illustrated in FIG. 14 in solid and dashed lines, respectively. As shown in FIGS. 13A and 13B, the translation of the follower nut 1130 along the shaft 1100 drives translation of the pushable actuation element 1150, which drives translation of the shuttle 1214.

As shown in FIG. 14, in some embodiments the follower nut 1130 may comprise one or more tabs 1132 that engage with one or more grooves 1104 in the shaft 1100. The grooves 1104 and tabs 1132 prevent the follower nut 1130 from rotating when the rotational actuation element 1120 rotates, while allowing the follower nut 1130 to translate long the shaft 1100. In other embodiments, different arrangements of engagement features may be used to guide and constrain the follower nut 1130. For example, ridges may be provided protruding from the shaft 1100 wall which engage grooves in the follower nut 1130. Although FIGS. 13A-14 illustrate the follower nut 1130 as having internal threads 1131 and the rotational actuation element 1120 as having external threads 1123, it should be understood that the reverse configuration could be used (i.e., the rotational actuation element 1120 having internal threads and the follower having external threads).

Figures 15A, 15B:
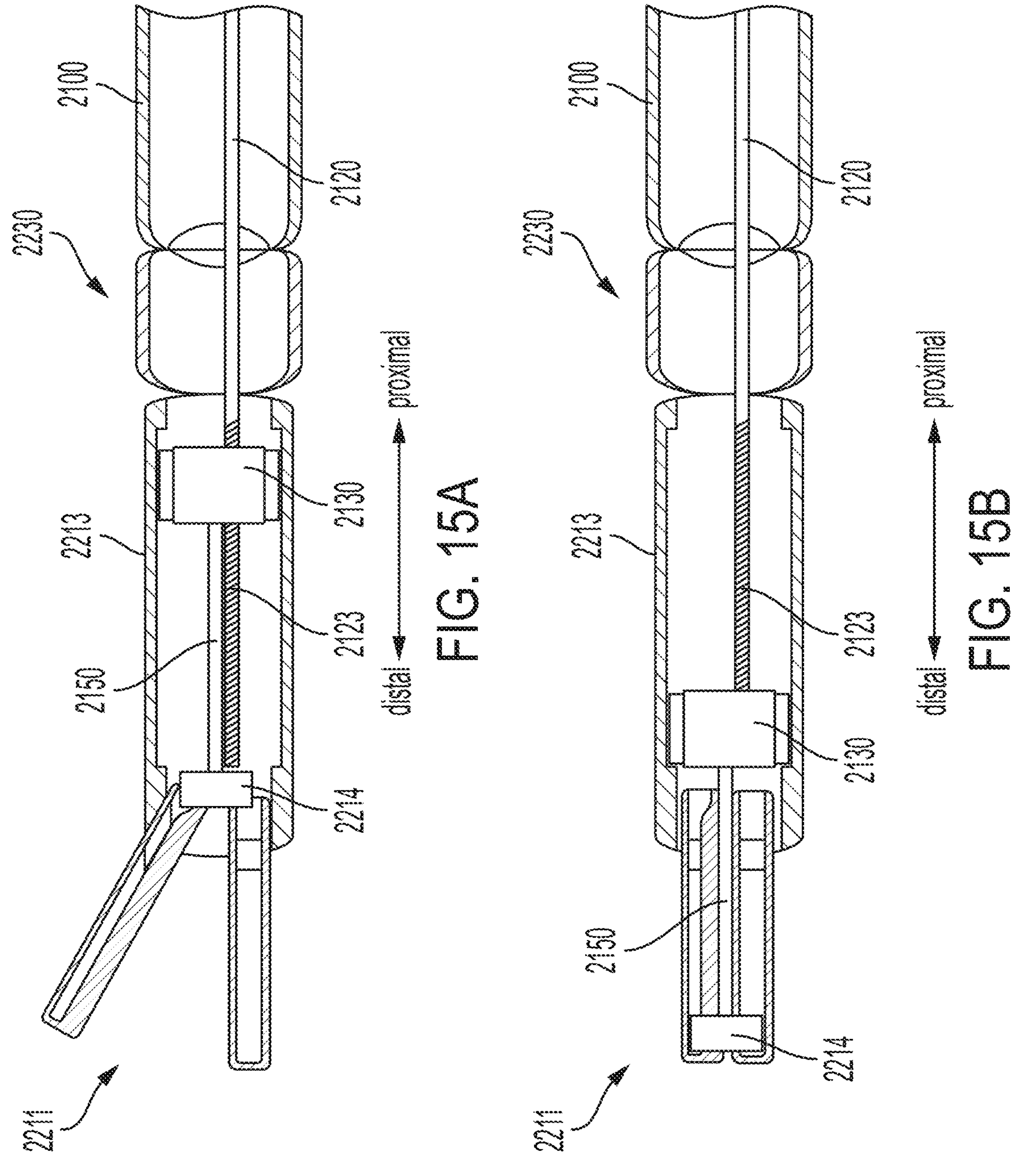
FIG. 15A is a schematic cross section of another embodiment of a distal portion of an instrument including the end effector in a first state, with the section taken along a longitudinal centerline of the end effector.
FIG. 15B is a schematic cross-section of the distal portion of the instrument of FIG. 15A with the end effector in a second state.

In FIGS. 13A and 13B, the follower nut 1130 is provided in the instrument shaft 1100, proximal of the articulable element 1230. In other embodiments, the follower nut could be provided elsewhere. For example, FIGS. 15A and 15B illustrate another embodiment that is similar to the embodiment of FIGS. 11-14, except that the follower nut 2130 is provided inside the clevis 2213 of the end effector 2210 instead of in the instrument shaft 2100. Thus, in this embodiment, the rotational actuation element 2120 extends through the articulable structure 2230. In some embodiments, a portion of the rotational actuation element 2120 that extends through the articulable structure 2230 may be laterally flexible in one or more lateral directions. In some embodiments, the pushable actuation element 2150 does not need to be (although it can be) laterally flexible, as it does not pass through the articulable structure 2230 in these embodiments.

Figures 16A, 16B:
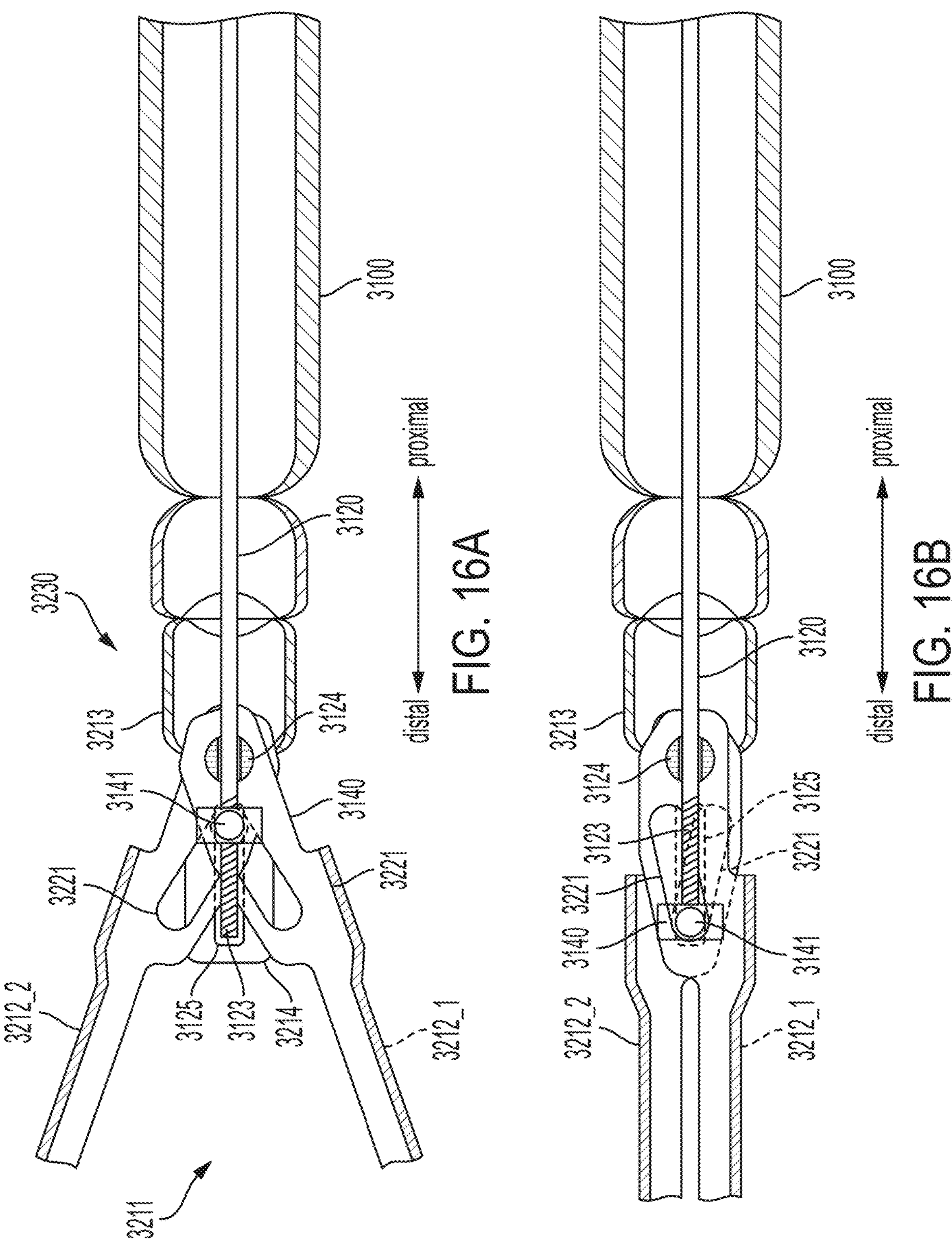
FIG. 16A is a cross section of yet another embodiment of distal portion of an instrument including the end effector in a first state, with the section taken along a longitudinal centerline of the end effector.
FIG. 16B is a cross section of the distal portion of the instrument of FIG. 16A with the end effector in a second state.

In the embodiments of FIGS. 11-15B, the rotational actuation element is coupled to a movable component of the end effector by a pushable actuation element, with a rotary-to-linear motion conversion mechanism coupling the pushable actuation element to the rotational actuation element. However, in other embodiments the rotational actuation element may be coupled directly to a movable component of the end effector without a pushable actuation element in between. For example, in FIGS. 16A and 16B an end effector 3210 is illustrated that comprises a jaw mechanism 3211 comprising jaw members 3212_1 and 3212_2. The jaw mechanism 3211 may be configured as a grasping device (e.g., forceps), a cutting device (e.g., scissors), an electrosurgical device, or any other device that utilizes a jaw mechanism 3211. FIGS. 16A and 16B comprise cross-sections taken along a longitudinal centerline of the end effector 3210 and shaft 3100. The jaw members 3212 are pivotably coupled to a clevis 3213 by a pin 3124. The clevis 3213 comprises two arms 3214 (only one visible in FIG. 16A) that extend along the proximal-distal direction on opposite side of the jaw members 3212. The arms 3214 comprise guide slots 3125 (only one visible in the FIG. 16A) extending along the proximal-distal direction. The end effector 3210 also comprises an actuation link 3140, with pins 3141 that extend laterally outward in opposite directions from one another to engage with the two guide slots 3125 of the arms 3214. The guide slots 3125 constrain the actuation link 3140 to allow only translational motion along the proximal-distal direction. The jaw members 3212 comprise ramps 3221, with the pins 3141 of the actuation link 3140 also being engaged with the ramps 3221. As the actuation link 3140 translates along the guide slot 3125, engagement between the pins 3141 and the ramps 3221 forces the jaw members 3212 to pivot. Specifically, translation of the actuation link 3140 in the distal direction causes closing of the jaw members 3212, while translation of the actuation link 3140 in the proximal direction causes opening of the jaw members 3212. FIG. 16A shows the jaw members 3212 in open positions and the actuation link 3140 at a most proximal position, while FIG. 16B shows the jaw members 3212 in a closed position and the actuation link 3140 at a most distal position.

As shown in FIGS. 16A and 16B, the actuation link 3140 is coupled with the rotational actuation element 3120. The actuation link 3140 comprises a bore with internal threads (not visible), and the rotational actuation link 3120 extends through the bore such that the internal threads of the actuation link 3140 engage with the external threads 3123 on the rotational actuation element 3120 such that rotation of the rotational actuation element 3120 drives translation of the actuation link 3140.

Various example embodiments of end effectors that may be used as the end effector 210 were described above, but it should be understood that other types of end effectors could be used as the end effector 210. In particular, any end effector that has a movable component that is configured to receive translational driving actuation can be used as the end effector 210, and a pushable actuation element may be coupled to the movable component to drive motion thereof (like the pushable actuation elements 1150 or 1250, for example) and a rotary-to-linear conversion mechanism (like the follower nut 1130 or 2130, for example) may be used to link the rotational actuation element 120 with the pushable actuation element. As described above, in such embodiments the rotary-to-linear conversion mechanism could be positioned proximally of an articulable structure (if present), or it could be positioned distally of an articulable structure (if present). The rotary-to-linear conversion mechanism could also be part of the end effector. Moreover, any end effector that has a movable component that is configured to receive rotational driving actuation can be used as the end effector 210, in which case the rotational actuation element 120 may be coupled directly with the movable component. In various embodiments portions (or the entirety) of the rotational actuation element 120, pushable actuation element (if present), or both are laterally flexible.

Manipulator System

Figure 17:
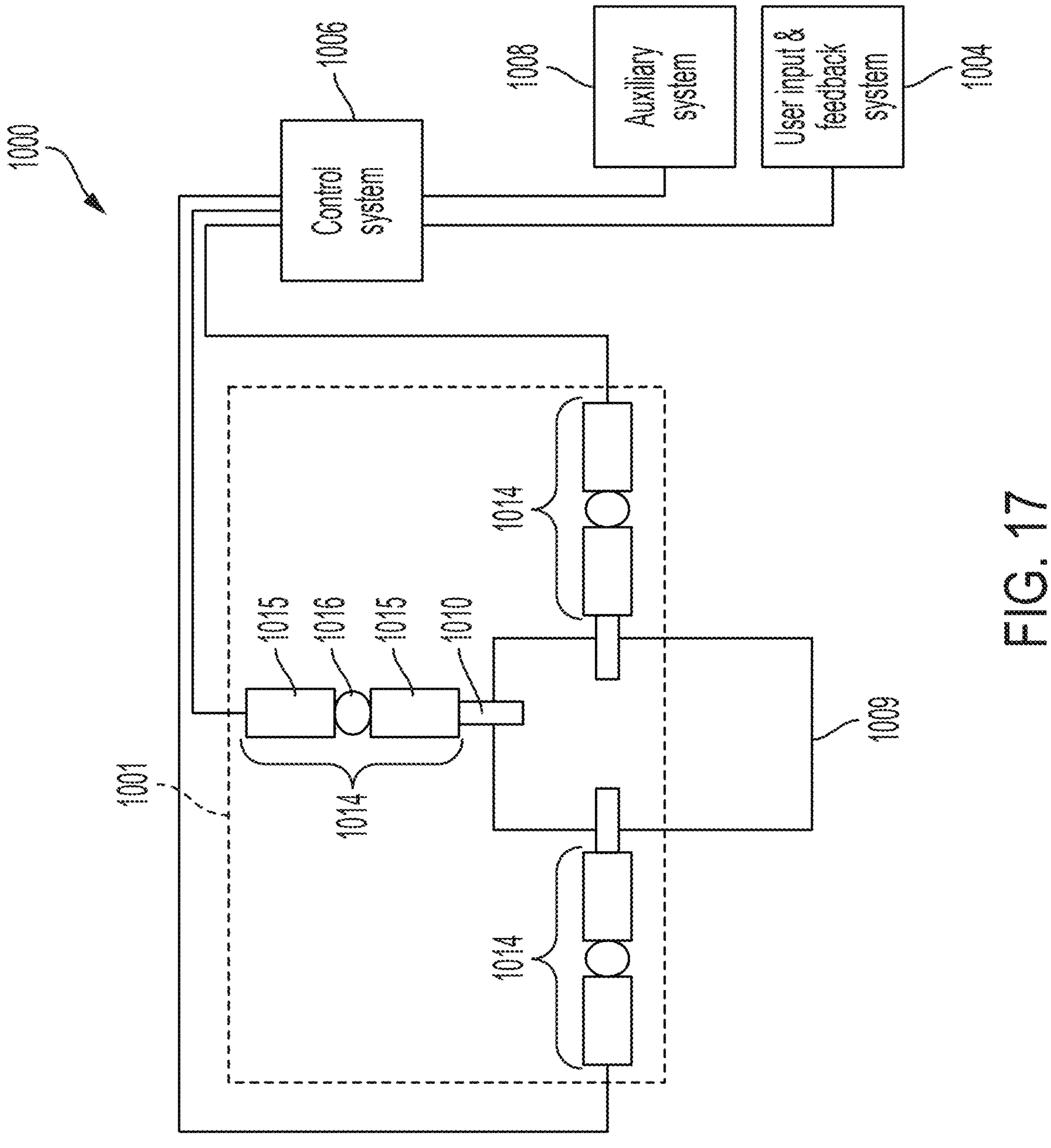
FIG. 17 is a schematic block diagram of an embodiment of a teleoperable manipulator system.

FIG. 17 is a schematic block diagram of an embodiment of a computer-assisted instrument control system 1000 for remote control of instruments in accordance with various embodiments, also referred to herein as a teleoperable instrument system. Such a system can be a medical system that employs robotic technology, as those having ordinary skill in the art are familiar with. The system 1000 comprises a manipulator assembly 1001, a control system 1006, and a user input and feedback system 1004. The system 1000 may also include an auxiliary system 1008 to provide various supporting functionality to the instruments or the overall system. These components of the system 1000 are described in greater detail blow.

The manipulator assembly 1001 comprises one or more manipulators 1014. FIG. 17 illustrates three manipulators 1014, but any number of manipulators 1014 may be included. While a manipulator may comprise a single mechanical link, in the embodiment of FIG. 17, each manipulator 1014 comprises a kinematic structure of two or more links 1015 coupled together by one or more joints 1016. The joints 1016 may impart various degrees of freedom of movement to the manipulator 1014, allowing the manipulator 1014 to be moved around a workspace 1009. For example, some joints 1016 may provide for rotation of links 1015 relative to one another, other joints 1016 may provide for translation of links 1015 relative to one another, and some may provide for both rotation and translation. Some or all of the joints 1016 may be powered joints, meaning a powered drive element may control movement of the joint 1016 through the supply of motive power. Such powered drive elements may comprise, for example, electric motors, pneumatic or hydraulic actuators, etc. Additional joints 1016 may be unpowered joints. FIG. 17 illustrates each manipulator 1014 as having two links 1015 and one joint 1016, but in practice a manipulator may include more links 1015 and more joints 1016, depending on the needs of the system 1000. The more links 1015 and joints 1016 are included, the greater the degrees of freedom of movement of the manipulator 1014.

Each manipulator 1014 may be configured to support and operate one or more instruments 1010. The instruments 1010 may include various types of instruments, including for example industrial instruments and medical instruments (e.g., surgical instruments, imaging instruments, diagnostic instruments, therapeutic instruments, etc.). For example, the instruments 1 and 10 described above may be used as any of the instruments 1010. A manipulator 1014 may comprise an instrument manipulator interface to which an instrument 1010 can be removably coupled. The instrument manipulator interface may be located, for example, at a distal end portion of the manipulator 1014. The instrument manipulator interface may include drive outputs to provide driving forces to drive inputs of the instrument 1010 to control operations of the instrument 1010, such as moving an end-effector of the instrument, opening/closing jaws, driving translating and/or rotating components, etc. The drive outputs may be driven by actuators (e.g., electrical motors, hydraulic actuators, pneumatic actuators, etc.) and may interface with and mechanically transfer driving forces to corresponding drive inputs of the instrument 1010 (directly, or via intermediate drive outputs, which may be part of a sterile instrument adaptor (ISA) (not illustrated)). The ISA may be placed between the instrument 1010 and the instrument interface to maintain sterile separation between the instrument 1010 and the manipulator 1014. The instrument interface may also comprise other interface components (not illustrated), such as electrical interfaces to provide and/or receive electrical signals to/from the instrument 1010. In some embodiments, the manipulator assembly can include flux delivery transmission capability as well, such as, for example, to supply electricity, fluid, vacuum pressure, light, electromagnetic radiation, etc. to the end effector. In other embodiments, such flux delivery transmission may be provided to an instrument through another auxiliary system, described further below.

Figure 18:
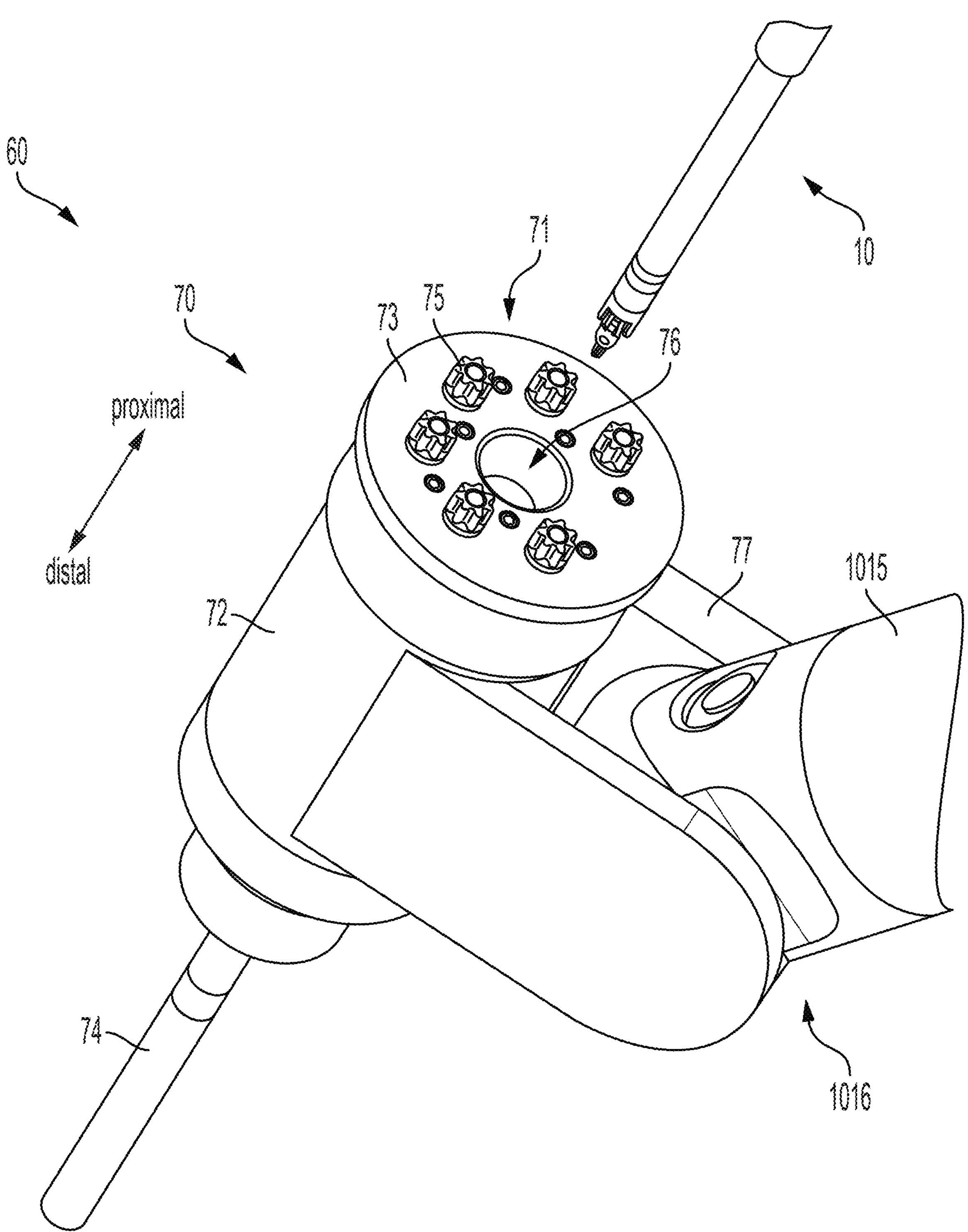
FIG. 18 is a partial, perspective view of an embodiment of an instrument manipulator.

An example embodiment of an instrument manipulating portion 60 of a manipulator 1014, is illustrated in FIG. 18. The instrument manipulating portion 60 is configured to support and operate an instrument 10 mounted thereon. As shown in FIG. 18, the instrument manipulating portion 60 comprises a base 77 and an instrument holder assembly 70. The base is coupled with a link 1015 of a manipulator 1014, for example by a joint 1016. The instrument holder assembly 70 comprises an outer housing 72 coupled to the base 77 and an instrument holder 71 coupled to the outer housing 72. The instrument holder 71 comprises an interface 73 and an inner portion (not illustrated) that is received within the outer housing 72. The instrument holder 71 may be rotatable relative to the outer housing 72, thus imparting a roll degree of freedom of motion to an instrument 10 mounted thereon.

As shown in FIG. 18, the instrument holder 71 comprises an interface 73 configured to receive and interface with the chassis 311 of the instrument 10 in a mounted state. The interface 73 comprises drive outputs 75 configured to interface with the drive inputs of the instrument, such as drive inputs 410 of the instrument 10, in a mounted state of the instrument to the manipulator. The drive outputs 75 may interface directly with the drive inputs 410, or the drive outputs 75 may interface indirectly with the drive inputs via intermediate drive outputs of an ISA (i.e., the drive outputs 75 engage corresponding intermediate drive outputs of the ISA, and the intermediate drive outputs of the ISA engage corresponding drive inputs 410). The drive outputs 75 may have a shape that is complementary to a shape of the drive inputs 410 and/or a shape of the intermediate drive outputs to allow for mating engagement such that rotation of the drive outputs 75 drives rotation drive inputs 410 and/or intermediate drive outputs. The inner portion of the instrument holder 71 may comprises actuators (not illustrated) coupled to the drive outputs 75 to supply torque to the drive outputs 75. Motive power, such as electricity or pressurized hydraulic or pneumatic fluid, may be provided to the actuators via power supply lines, which may be routed through the base 77 and into the housing 72.

The instrument holder assembly 70 of the embodiment of FIG. 18 comprises a passage 76 extending through the instrument interface 73 and the outer housing 72. In FIG. 25, the passage 76 comprises a generally cylindrical bore, but in other embodiments the passage 76 may have other shapes, such as a slot with a U-shaped cross-section that is open along a lateral side of the instrument holder assembly 70 in addition to being open at opposite axial ends of the instrument holder assembly 70. A portion of the shaft 100 and the sleeve 312 are received in the passage 76 in the mounted state. As described above, the sleeve 312 comprises alignment features 316*a* and 316*b*, and the inner surface of the passage 76 may comprise complementary alignment features (not illustrated) to engage with the alignment features 316*a* and 316*b* so as to progressively align the instrument 10 as the sleeve 312 is inserted farther into the passage 76.

As shown in FIG. 18, a cannula 74 may be coupled to (or may be an integral part of) the instrument manipulating portion 60. The cannula 74 may be configured for insertion into a patient through an incision or natural orifice so as to allow the shaft 100 of the instrument to be inserted and advanced therethrough. As noted above, a distal end portion of the sleeve 312 of an instrument 10 may extend partially into the cannula 74, and a seal may be provided between the cannula 74 and the exterior of the sleeve 312.

The system 1000 can also include a user input and feedback system 1004 operably coupled to the control system 1006. The user input and feedback system 1004 comprises one or more input devices to receive input control commands to control operations of the manipulator assembly 1001. Such input devices may include but are not limited to, for example, telepresence input devices, triggers, grip input devices, buttons, switches, pedals, joysticks, trackballs, data gloves, trigger-guns, gaze detection devices, voice recognition devices, body motion or presence sensors, touchscreen technology, or any other type of device for registering user input. In some cases, an input device may be provided with the same degrees of freedom as the associated instrument that they control, and as the input device is actuated, the instrument, through drive inputs from the manipulator assembly, is controlled to follow or mimic the movement of the input device, which may provide the user a sense of directly controlling the instrument. Telepresence input devices may provide the operator with telepresence, meaning the perception that the input devices are integral with the instrument. The user input and feedback system 1004 may also include feedback devices, such as a display device (not shown) to display images (e.g., images of the workspace 1009 as captured by one of the instruments 1010), haptic feedback devices, audio feedback devices, other graphical user interface forms of feedback, etc.

The control system 1006 may control operations of the system 1000. In particular, the control system 1006 may send control signals (e.g., electrical signals) to the manipulator assembly 1001 to control movement of the joints 1016 and to control operations of the instruments 1010 (e.g., through drive interfaces at the manipulators 1014). In some embodiments, the control system 1006 may also control some or all operations of the user input and feedback system 1004, the auxiliary system 1008, or other parts of the system 1000. The control system 1006 may include an electronic controller to control and/or assist a user in controlling operations of the manipulator assembly 1001. The electronic controller comprises processing circuitry configured with logic for performing the various operations. The logic of the processing circuitry may comprise dedicated hardware to perform various operations, software (machine readable and/or processor executable instructions) to perform various operations, or any combination thereof. In examples in which the logic comprises software, the processing circuitry may include a processor to execute the software instructions and a memory device that stores the software. The processor may comprise one or more processing devices capable of executing machine readable instructions, such as, for example, a processor, a processor core, a central processing unit (CPU), a controller, a microcontroller, a system-on-chip (SoC), a digital signal processor (DSP), a graphics processing unit (GPU), etc. In examples in which the processing circuitry includes dedicated hardware, in addition to or in lieu of the processor, the dedicated hardware may include any electronic device that is configured to perform specific operations, such as an Application Specific Integrated Circuit (ASIC), a Field Programmable Gate Array (FPGA), a Complex Programmable Logic Device (CPLD), discrete logic circuits, a hardware accelerator, a hardware encoder, etc. The processing circuitry may also include any combination of dedicated hardware and processor plus software.

As noted above, differing degrees of user control versus autonomous control may be utilized in the system 1000, and embodiments disclosed herein may encompass fully user-controlled systems, fully autonomously-controlled systems, and systems having any combination of user and autonomous control. For operations that are user-controlled, the control system 1006 generates control signals in response to receiving a corresponding user input command via the user input and feedback system 1004. For operations that are autonomously controlled, the control system 1006 may execute pre-programmed logic (e.g., a software program) and may determine and send control commands based on the programming (e.g., in response to a detected state or stimulus specified in the programming). In some systems, some operations may be user controlled and others autonomously controlled. Moreover, some operations may be partially user controlled and partially autonomously controlled—for example, a user input command may initiate performance of a sequence of events, and then the control system 1006 may perform various operations associated with that sequence without needing further user input.

While the control system 1006 is illustrated as a separate element in FIG. 17, those having ordinary skill in the art would understand that the control system 1006 may be a distributed system, or portions thereof may be, among one or more of the auxiliary system 1008, the user input and feedback system 1004, and the manipulator system 1001.

The auxiliary system 1008 may comprise various auxiliary devices that may be used in operation of the system 1000. For example, the auxiliary system 1008 may include power supply units, auxiliary function units (e.g., functions such as irrigation, evacuation, energy supply, illumination, sensors, imaging, etc.). As one example, in a system 1000 for use in a medical procedure context, the auxiliary system 1008 may comprise a display device for use by medical staff assisting a procedure, while the user operating the input devices may utilize a separate display device that is part of the user input and feedback system 1004. As another example, in a system 1000 for use in a medical context, the auxiliary system 1008 may comprise flux supply units that provide surgical flux (e.g., electrical power) to instruments 1010. An auxiliary system 1008 as used herein may thus encompass a variety of components and does not need to be provided as an integral unit.

The embodiments described herein (including the instrument 10 and system 1000 described above) may be well suited for use in medical applications. In particular, some embodiments are suitable for use in, for example, surgical, teleoperated surgical, diagnostic, therapeutic, and/or biopsy procedures. Such procedures could be performed, for example, on human patients, animal patients, human cadavers, animal cadavers, and portions or human or animal anatomy. Some embodiments may also be suitable for use in, for example, for non-surgical diagnosis, cosmetic procedures, imaging of human or animal anatomy, gathering data from human or animal anatomy, training medical or non-medical personnel, and procedures on tissue removed from human or animal anatomies (without return to the human or animal anatomy). Even if suitable for use in such medical procedures, the embodiments may also be used for benchtop procedures on non-living material and forms that are not part of a human or animal anatomy. Moreover, some embodiments are also suitable for use in non-medical applications, such as industrial robotic uses, and sensing, inspecting, and/or manipulating non-tissue work pieces. In non-limiting embodiments, the techniques, methods, and devices described herein may be used in, or may be part of, a computer-assisted medical system employing robotic technology such as the da Vinci® Surgical Systems commercialized by Intuitive Surgical, Inc., of Sunnyvale, California. Those skilled in the art will understand, however, that aspects disclosed herein may be embodied and implemented in various ways and systems, including manually operated instruments and computer-assisted, teleoperated systems, in both medical and non-medical applications. Reference to the daVinci® Surgical Systems are illustrative and not to be considered as limiting the scope of the disclosure herein.

It is to be understood that both the general description and the detailed description provide example embodiments that are explanatory in nature and are intended to provide an understanding of the present disclosure without limiting the scope of the present disclosure. Various mechanical, compositional, structural, electrical, and operational changes may be made without departing from the spirit and scope of this description and the claims. In some instances, well-known circuits, structures, and techniques have not been shown or described in detail in order not to obscure the embodiments. Like numbers in two or more figures represent the same or similar elements.

Further, the terminology used herein to describe aspects of the invention, such as spatial and relational terms, is chosen to aid the reader in understanding example embodiments of the invention but is not intended to limit the invention. For example, spatially terms-such as "beneath", "below", "lower", "above", "upper", "proximal", "distal", "up", "down", and the like—may be used herein to describe directions or one element's or feature's spatial relationship to another element or feature as illustrated in the figures. These spatial terms are used relative to the figures and are not limited to a particular reference frame in the real world. Thus, for example, the direction "up" in the figures does not necessarily have to correspond to an "up" in a world reference frame (e.g., away from the Earth's surface). Furthermore, if a different reference frame is considered than the one illustrated in the figures, then the spatial terms used herein may need to be interpreted differently in that different reference frame. For example, the direction referred to as "up" in relation to one of the figures may correspond to a direction that is called "down" in relation to a different reference frame that is rotated 180 degrees from the figure's reference frame. As another example, if a device is turned over 180 degrees in a world reference frame as compared to how it was illustrated in the figures, then an item described herein as being "above" or "over" a second item in relation to the Figures would be "below" or "beneath" the second item in relation to the world reference frame. Thus, the same spatial relationship or direction can be described using different spatial terms depending on which reference frame is being considered. Moreover, the poses of items illustrated in the figure are chosen for convenience of illustration and description, but in an implementation in practice the items may be posed differently.

In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components, unless specifically noted otherwise. Mathematical and geometric terms are not necessarily intended to be used in accordance with their strict definitions unless the context of the description indicates otherwise, because a person having ordinary skill in the art would understand that, for example, a substantially similar element that functions in a substantially similar way could easily fall within the scope of a descriptive term even though the term also has a strict definition.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

Unless otherwise noted herein or implied by the context, when terms of approximation such as "substantially," "approximately," "about," "around," "roughly," and the like, are used in conjunction with a stated numerical value, property, or relationship, such as an end-point of a range or geometric properties/relationships (e.g., parallel, perpendicular, straight, etc.), this should be understood as meaning that mathematical exactitude is not required for the value, property, or relationship, and that instead a range of variation is being referred to that includes but is not strictly limited to the stated value, property, or relationship. In particular, the range of variation around the stated value, property, or relationship includes at least any inconsequential variations from the value, property, or relationship, such as variations that are equivalents to the stated value, property, or relationship. The range of variation around the stated value, property, or relationship also includes at least those variations that are typical in the relevant art for the type of item in question due to manufacturing or other tolerances.

As used herein, "transverse" refers to a positional relationship of two items in which one item is oriented crosswise at an angle relative to the other item, such as being substantially or generally perpendicular to the other item. As used herein, "transverse" includes, but does not require, an exactly perpendicular relationship. For example, unless otherwise noted herein or implied by the context, "transverse" may include at least positional relationships in which one item is oriented at nonparallel angle to the other item, such as for example, an angle ranging from 45° to 135° relative to the other item.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A medical instrument comprising:

an instrument shaft;

a movable component coupled to the instrument shaft;

a rotational actuation element extending through the instrument shaft and operably coupled to the movable component; and a transmission assembly movably coupled to the instrument shaft and comprising:

a first drive member configured to drive translation of the instrument shaft relative to the transmission assembly; and a second drive member coupled to the rotational actuation element and configured to drive rotation of the rotational actuation element;

wherein translation of the instrument shaft relative to the transmission assembly causes translation of the rotational actuation element relative to the transmission assembly.

2. The medical instrument of claim 1, further comprising:

a gear assembly coupled to the rotational actuation element, wherein the second drive member comprises a drive shaft coupled to the gear assembly such that rotation of the drive shaft drives rotation of the rotational actuation element.

3. The medical instrument of claim 2, wherein:

the gear assembly comprises a first gear coupled to the drive shaft and a second gear coupled to the rotational actuation element; and the first gear is translatable along the drive shaft.

4. The medical instrument of claim 3, wherein:

translation of the instrument shaft relative to the transmission assembly causes translation of the first gear along the drive shaft.

5. The medical instrument of claim 2, further comprising:

a gear housing coupled to a proximal portion of the instrument shaft and housing the gear assembly.

6. The medical instrument of claim 1, further comprising:

an end effector coupled to a distal end of the instrument shaft, wherein the movable component comprises a portion of the end effector.

7. The medical instrument of claim 6, wherein:

the end effector comprises a jaw mechanism and the movable component comprises a translatable component coupled to drive opening and closing motion of the jaw mechanism.

8. The medical instrument of claim 7, wherein:

the end effector comprises a stapler and the movable component comprises a staple firing mechanism translatable relative to the jaw mechanism to drive opening and closing of the jaw mechanism and firing of staples.

9. The medical instrument of claim 6, further comprising:

a pushable actuation element; and a rotary-to-linear motion conversion mechanism, wherein:

the portion of the end effector comprises a translatable component coupled to the pushable actuation element; and the rotational actuation element is coupled to the pushable actuation element by the rotary-to-linear motion conversion mechanism such that rotation of the rotational actuation element drives translation of the translatable component.

10. The medical instrument of claim 6, wherein the portion of the end effector is coupled directly with the rotational actuation element.

11. The medical instrument of claim 10, wherein:

the end effector comprises a jaw mechanism and the portion of the end effector is an actuation link configured to drive motion of the jaw mechanism.

12. The medical instrument of claim 1, further comprising:

a plurality of pullable actuation elements;

wherein:

the first drive member comprises a drum; and the plurality of pullable actuation elements are coupled to the drum and to the instrument shaft such that rotation of the drum drives translation of the instrument shaft relative to the transmission assembly.

13. The medical instrument of claim 12, wherein the movable component is a first movable component and the medical instrument further comprises:

a second movable component coupled to the instrument shaft;

wherein:

a first pullable actuation element of the plurality of pullable actuation elements is coupled to the second movable component and to the drum; and the transmission assembly further comprises a third drive member configured to actuate the first pullable actuation element to drive a degree of freedom of motion of the second movable component.

14. The medical instrument of claim 13, wherein the third drive member comprises an actuation transfer mechanism coupled to the first pullable actuation element such that the first pullable actuation element is independently actuatable by the third drive member and the first drive member.

15. The medical instrument of claim 13, wherein the second movable component comprises an articulable structure.

16. The medical instrument of claim 15, wherein the rotatable rotational actuation element extends through the articulable structure.

17. The medical instrument of claim 15, wherein the rotatable rotational actuation element is coupled to a pushable actuation element that extends through the articulable structure.

18. A method of operating a medical instrument comprising an instrument shaft, a transmission assembly, and a movable component, the method comprising:

causing motion of the instrument shaft relative to the transmission assembly by driving a first drive member of the transmission assembly; and causing motion of the movable component by driving a second drive member of the transmission assembly to rotate a rotational actuation element that extends through the instrument shaft and is operably coupled to the movable component;

wherein translation of the instrument shaft relative to the transmission assembly causes translation of the rotational actuation element relative to the transmission assembly.

19. The method of claim 18, wherein:

driving the second drive member of the transmission assembly to rotate the rotational actuation element comprises causing a drive shaft of the second drive member to rotate, the drive shaft operably coupled to the rotational actuation element by a gear assembly coupled to the instrument shaft; and the translation of the instrument shaft relative to the transmission assembly causes translation of the gear assembly along the drive shaft.

20. The method of claim 18, wherein:

causing motion of the movable component comprises converting rotation of the rotational actuation element into translation of the movable component.

* * * * *